United States Patent
Braginsky et al.

(10) Patent No.: US 6,938,755 B2
(45) Date of Patent: Sep. 6, 2005

(54) PACKAGE FOR DISPENSING AND STORING OF SURGICAL MEDICAL DEVICES AND METHODS RELATED THERETO

(76) Inventors: Michael Braginsky, 26 Hamlet St., Newton, MA (US) 02459; Joan Goldberg, 146 Colonial Dr., Somerset, MA (US) 02726; Shelby Cook, 2 Carlow Crossing, Mansfield, MA (US) 02048; Donna Raiche, 189 Lamphor St., Fall River, MA (US) 02721; Michael A. Valerio, 44 Ray Rd., Wrentham, MA (US) 02093

( * ) Notice: Subject to any disclaimer, the term of this patent is extended or adjusted under 35 U.S.C. 154(b) by 152 days.

(21) Appl. No.: 10/420,993

(22) Filed: Apr. 22, 2003

(65) Prior Publication Data

US 2004/0020795 A1 Feb. 5, 2004

Related U.S. Application Data

(63) Continuation of application No. 09/411,411, filed on Oct. 1, 1999, now abandoned.

(51) Int. Cl.[7] ............................................. A61B 17/06
(52) U.S. Cl. ...................... 206/63.3; 206/363; 206/523
(58) Field of Search ................. 206/570, 363, 206/438, 366, 388, 63.3, 523, 227, 380, 382

(56) References Cited

U.S. PATENT DOCUMENTS

| | | | | |
|---|---|---|---|---|
| 324,557 A | * | 8/1885 | Holzgens | 206/380 |
| 3,280,971 A | * | 10/1966 | Regan, Jr. | 206/63.3 |
| 3,985,227 A | * | 10/1976 | Thyen et al. | 206/63.3 |
| 4,391,365 A | * | 7/1983 | Batchelor | 206/63.3 |
| 5,197,597 A | * | 3/1993 | Leary et al. | 206/63.3 |
| 5,582,288 A | * | 12/1996 | Zatarga | 206/63.3 |
| 5,601,185 A | * | 2/1997 | Behring et al. | 206/63.3 |
| 5,871,089 A | * | 2/1999 | Odermatt | 206/63.3 |
| 6,029,806 A | * | 2/2000 | Cerwin et al. | 206/63.3 |

* cited by examiner

Primary Examiner—Shian T. Luong
(74) Attorney, Agent, or Firm—Baker & Hostetler LLP

(57) ABSTRACT

Featured is a package or carrier for releasably holding any of a number of medical devices including a rigid member that is interconnected to a flexible member such as suture-needle combinations. The package includes a support unit having a long axis, which support unit is configured so as to include a handle/cover member, a face cover member, a stationary panel, a plurality of folding panels, and a plurality (i.e., two or more) of securing members that releasably secure or retain portions of the medical device and/or portions of the interconnected flexible member to the package. The handle/cover member is foldable in either of two positions. In the first position a part of the handle/cover member covers a portion of the stationary panel that is not covered by the face cover member. In the second position, this portion of the stationary panel becomes uncovered to expose the medical devices that are secured therein and. When the handle cover member is folded into the second position, it also is relocated so as to create a handle for the package and so a portion of the rigid member extends beyond an edge of the open package. The support unit can further include thereon a mounting member to releasably retain the rigid member. Also featured are medical device kits embodying such a package, a method for dispensing medical devices or sutures using such a package and methods related thereto.

63 Claims, 13 Drawing Sheets

US 6,938,755 B2

PACKAGE FOR DISPENSING AND STORING OF SURGICAL MEDICAL DEVICES AND METHODS RELATED THERETO

This application is a continuation of 09/411,411 filed on Oct. 1, 1999, now abandoned.

FIELD OF INVENTION

The present invention relates to the packaging for a medical device that is interconnected to a flexible component including for example, bundled ligatures, looped sutures, double-armed sutures, double-stranded needles, braided steel and dialysis cuffs as well as medical device kits employing such packaging and methods related thereto.

BACKGROUND OF THE INVENTION

There are a number of types of packages for sutures and combined surgical needle-suture devices known in the art. Generally, such a package should be constructed to adequately secure a needle and suture while allowing easy withdrawal during use. It also is preferable to design and construct the package in accordance with its intended application. For example, suture packages must often accommodate suture material of high quality generally having a surgical needle at one end, all in a readily dispensable fashion so as to have optimum handling characteristics. Cardiovascular sutures are generally "double armed", that is a needle is provided at each end of the suture, which presents still additional packaging difficulties. Moreover, in cardiovascular applications differently colored sutures are used for identification purposes.

Generally, the needle-suture devices of a cardiovascular suture package must be secured in spaced relation such that during a critical procedure such as a bypass operation, the surgeon can readily grasp the needle with his forceps or other means known in the art and quickly remove the suture from the package without difficulty. Because of the size of typical prior art suture packages, the scrub nurse typically holds the suture package away from the surgical or sterile field so as to avoid interfering with the surgeon's view of the surgical field. As a consequence, the scrub nurse usually has to remove a needle with the suture and hand it over to the surgeon and thus effectively increasing the time required to perform the procedure.

A customary practice in cardiovascular surgery also is to attach a pledget to the center of the suture. In such applications, a pledget is a small pad or cushion used to distribute the force of the sterile suture over a greater area of tissue to prevent cutting the relatively delicate tissue with the fine denier suture. In cardiovascular surgery one typical pledget is formed of PTFE felt.

Thus, a suture package for such cardiovascular sutures also is constructed in a manner which stores the sterile suture with both needles, as well as the pledget. Additionally, the package is constructed to be opened and the needle-suture-pledget device removed without entanglement of the pledget with the suture or the suture upon itself.

It thus would be desirable to provide a new package for suture/needle combinations as well as for any of a number of medical devices including a rigid member interconnected to a flexible member that would allow the package to be located more proximal to the surgical field as compared to prior art packages as well as a suture kit employing such a package and methods related thereto. It is particularly desirable to provide such a package for medical devices in general and more specifically suture/needle combinations that would be smaller in overall dimension when in the stored configuration as compared to prior art packages and kits.

It also is desirable to provide a package that can be reconfigured from the stored configuration to create a handle that a user may grasp or hold while withdrawing the contents of the package. More particularly, to create a handle so that the grasping or holding by the user does not impede withdrawal of the package's contents. When so reconfigured, the package also is configured so as to provide good access to, the medical device rigid member, for example a needle that is attached to a suture, so that the rigid member can be easily grasped by the user for its withdrawal from the package. Moreover, it is desirable to provide a package that is simple in construction and more user friendly as compared to prior art devices while assuring that sutures and pledgets or other medical devices can be removed therefrom without becoming entangled when being removed from the packaging.

SUMMARY OF THE INVENTION

The present invention features a novel package or carrier for releasably retaining any of a number of medical devices including a rigid member that is interconnected to a flexible member. Such medical device products include, but are not limited to, bundled ligatures (i.e., long strands of suture ties with clips thereon), double stranded needles, or double armed sutures, single stranded needles, looped sutures, braided steel and dialysis cuffs. The package or carrier of the present invention is particularly advantageous for releasably retaining or holding a suture, having a needle at least at one end thereof, and more particularly for releasably retaining a plurality of cardiovascular double-armed sutures in seriatim or series with a pledget disposed between each pair of needles. Also featured is a medical device kit, such as a suture kit, embodying such a novel package, a method for dispensing medical devices or sutures using such a kit and other methods related thereto.

In a broad aspect, the package of the present invention includes a support unit having a long axis and a plurality of fold lines, some transverse to the long axis, hereinafter transverse fold lines and some parallel to the long axis, hereinafter side fold lines. The support unit also is generally configured so as to include a handle/cover member, a face cover member, a stationary panel, a plurality of folding panels, and a plurality (i.e., two or more) of securing members that releasably secure or retain portions of the medical device and/or portions of the interconnected flexible member to the package. The support unit can further include thereon a foam mounting strip or other means known in the art to releasably retain the medical device rigid member (e.g. needle) that is interconnected to the flexible member.

The stationary panel includes a cover securing mechanism to secure the face cover member and is pivotably connected to each of the face cover member and the handle/cover member by a first side fold line and a first transverse fold line respectively. The face cover member also is folded about the first side fold line so the face cover member is disposed over a portion of the stationary panel and is secured to the stationary panel by the cover securing mechanism.

The handle/cover member is foldable in either of two positions. In the first position a part of the handle/cover member forms a cover over the portion of the stationary panel that is not covered by the face cover member. When the handle/cover member is folded in the second position, this portion of the stationary panel becomes uncovered to expose the medical devices that are secured therein, for example the needles of a suture product on the foam mounting strip, for removal therefrom. When the handle cover member is folded into the second position, it also is relocated so a part of the handle/cover member is proximal a back surface of the stationary panel and preferably another part thereof is proximal the back surface of the face cover member to create a handle for the package. Additionally, the handle can be configured to include a handle extension so the package can be located a distance away from the person holding the package during the medical or surgical procedure.

In a particular embodiment, the handle/cover member includes an arcuate or other shape segment along an edge opposite the first transverse fold line and the face cover member includes an extension segment that extends along the long axis in a direction opposite to first transverse fold line. When the handle/cover member is folded in the second position, the arcuate or other shape segment and the face cover member extension segment also are proximal to each other thereby creating a handle.

When using prior art carriers or packages, the user's normal tendency is to grab the package or carrier at the center of the package. This action pinches the package thereby causing difficulties in removing the sutures. In contrast, the handle created by the folding of the handle/cover member into the second position, avoids this problem because the sutures do not pass through the area of the handle.

When the handle/cover member is folded in the second position, the exposed medical device rigid members (e.g., needles) also are preferably presented so the user (e.g., surgeon or nurse) has much better access to the rigid member as compared to prior art packages. More particularly, the handle/cover member is configured so the medical device rigid member (e.g. needles) extends beyond the end or confines of the package when the handle/cover member is in the second position. This is particularly advantageous for suture-needle combinations, because these feature in combination with the compact size of the package of the present allows the open end of the package to be positioned immediately adjacent to the surgical field, thus allowing the surgeon to continually pull the needle(s) and suture(s) from the package as the surgeon is performing the procedure. Because of the compact size of the package of the present invention, it is also possible to position the entire package in the sterile field without significantly affecting the surgeon's view or access.

According to one aspect of the present invention, the plurality of securing members comprises a plurality of pairs of through apertures being arranged in the flat unit so as to form at least two rows of through apertures. Each row is arranged so as to be generally transverse to the long axis and so as to include at least one of the plurality of through aperture pairs. The rows also are arranged so that one row is disposed in the stationary panel and the other row, the second row, is disposed in one of the plurality of folding panels, preferably the second folding panel.

In more specific embodiments, the plurality of securing members further comprises a third or intermediate row of at least one through aperture pair. The intermediate row is disposed in the stationary panel and spaced from the first row so as to be disposed between the first and second rows of the at least one through apertures. Also, each row can include a plurality of through aperture pairs. Additionally, the through aperture pairs of the at least two rows, or the three rows, are further arranged so as to form at least one column of through aperture pairs and more particularly a plurality of such columns, each column being generally parallel to the long axis.

The plurality of securing members can further comprise a multiplicity (i.e., four or more) of such rows and/or the flat unit can be arranged so as to further included a multiplicity of folding panels. In more particular embodiments, the fourth and subsequent row of the at least one through aperture pair are disposed in one of the folding panels, such as one of the added panels. Preferably the folding panels are added in pairs, where one folding panel of each added pair includes the additional row of at least one through aperture pair and the other folding panel of the pair does not include through aperture pairs.

According to another aspect of the present invention, the plurality of securing members comprises a plurality of through apertures and a plurality of tabs, where each tab is disposed with respect to one of the plurality of through apertures so as to subdivided the through aperture into two through openings. The plurality of tabs and through apertures are arranged in the flat unit so as to form at least two rows of such through apertures and tabs. Each row is arranged so as to be generally transverse to the long axis and so as to include at least one of the plurality of through apertures and tabs. The rows also are arranged so that one row is disposed in the stationary panel and the other row, the second row, is disposed in one of the plurality of folding panels, preferably the second folding panel.

In more specific embodiments, the plurality of securing members further comprises a third or intermediate row of at least one through aperture and tab. The intermediate row is disposed in the stationary panel and spaced from the first row so as to be disposed between the first and second rows of the at least one through aperture and tab. Also, each row can include a plurality of through apertures and tabs. Additionally, the through apertures and tabs of the at least two rows, or the three rows, are further arranged so as to form at least one column thereof and more particularly a plurality of such columns, each column being generally parallel to the long axis.

The plurality of securing members can further comprise a multiplicity (i.e., four or more) of such rows and/or the flat unit can be arranged so as to further included a multiplicity of folding panels. In more particular embodiments, the fourth and subsequent row is disposed in one of the folding panels, such as one of the added panels. Preferably the folding panels are added in pairs, where one panel of the pair includes the added row of the at least one through aperture and tab and the other panel is without such through apertures and tabs.

With the above-describe arrangements, the flexible component of the medical device may be withdrawn successively without entanglement from each of the plurality of securing members or from that, which more specifically comprises the plurality of securing members.

Other aspects and embodiments of the invention are discussed below.

DEFINITIONS

The instant invention is most clearly understood with reference to the following definitions:

A double stranded device shall be understood to mean a device having a pair of flexible members from a single rigid member, such as for example a pair of sutures attached to a single needle.

A double armed device shall be understood to mean a device having a flexible member extending between two rigid members, such as for example, a suture extending between two needles.

A single armed device shall be understood to mean a device having a flexible member attached to a rigid member, such as for example, a suture attached to a single needle.

BRIEF DESCRIPTION OF THE DRAWING

For a fuller understanding of the nature and desired objects of the present invention, reference is made to the following detailed description taken in conjunction with the accompanying drawing figures wherein like reference characters denote corresponding parts throughout the several views and wherein.

DESCRIPTION OF THE PREFERRED EMBODIMENT

Figure 1A:
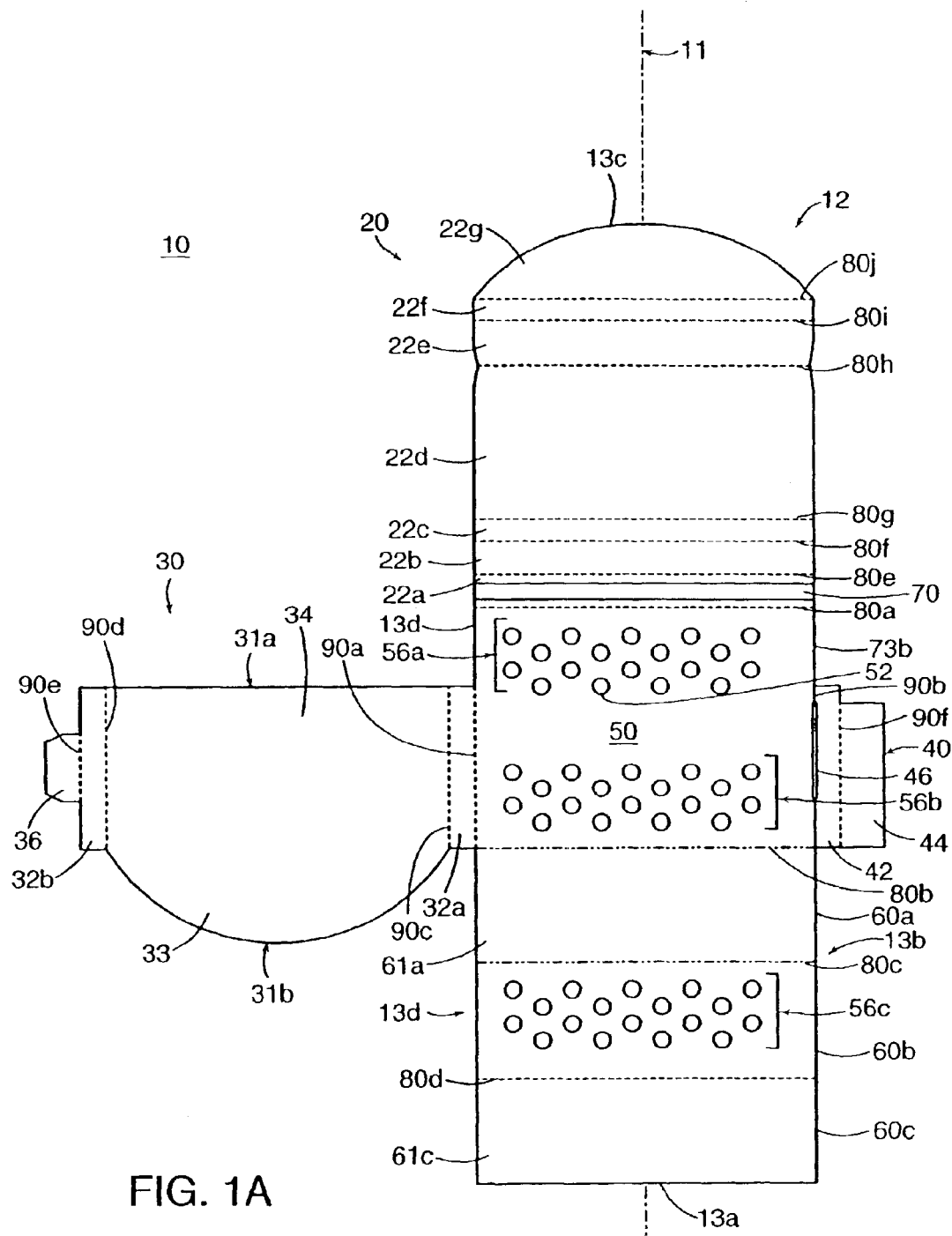
FIG. 1A is a plan view of one embodiment of a package according to the present invention with the sutures and needles removed for clarity.
Figure 1B:
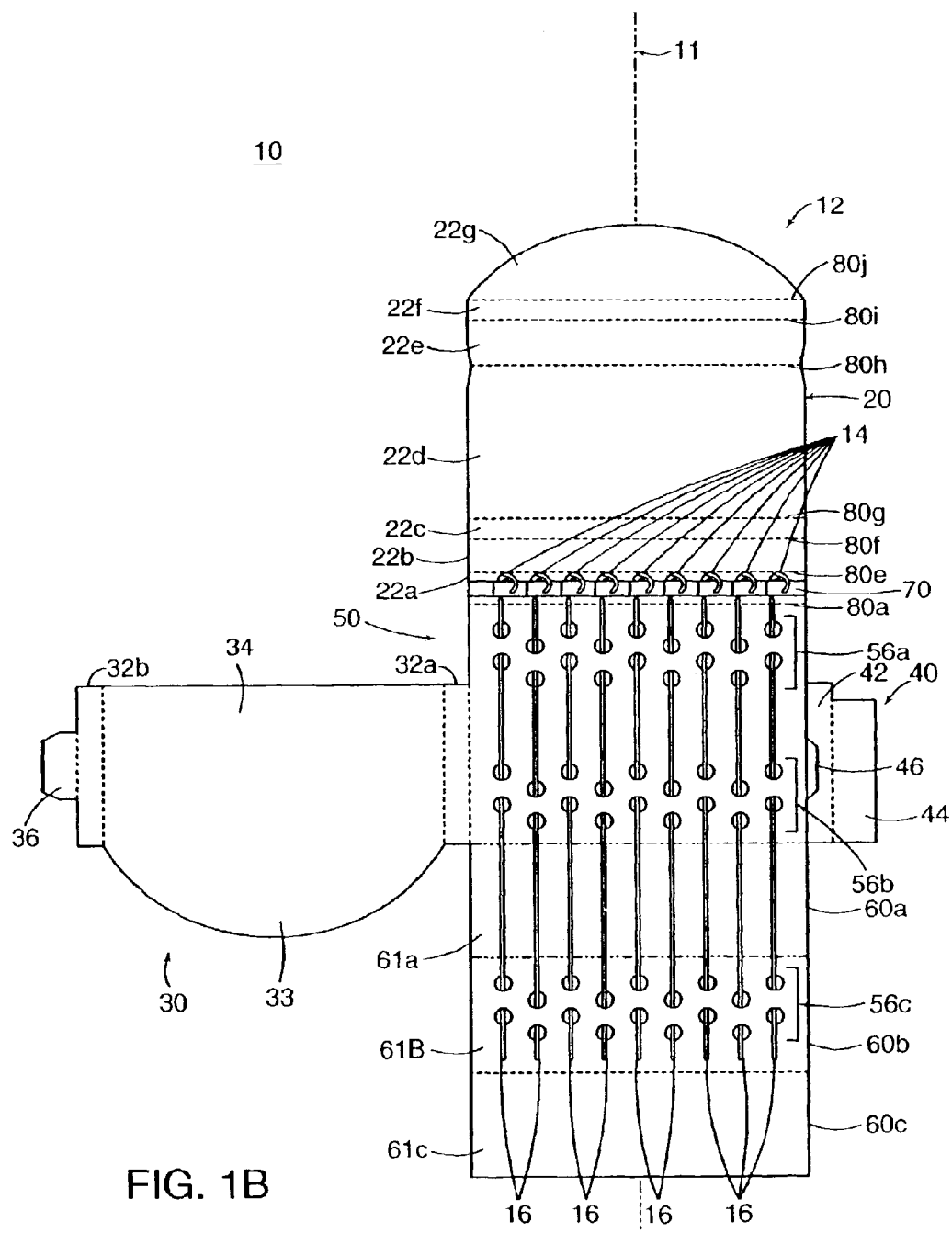
FIG. 1B is another plan view of the package of FIG. 1A with the sutures and needles loaded therein.
Figure 1C:
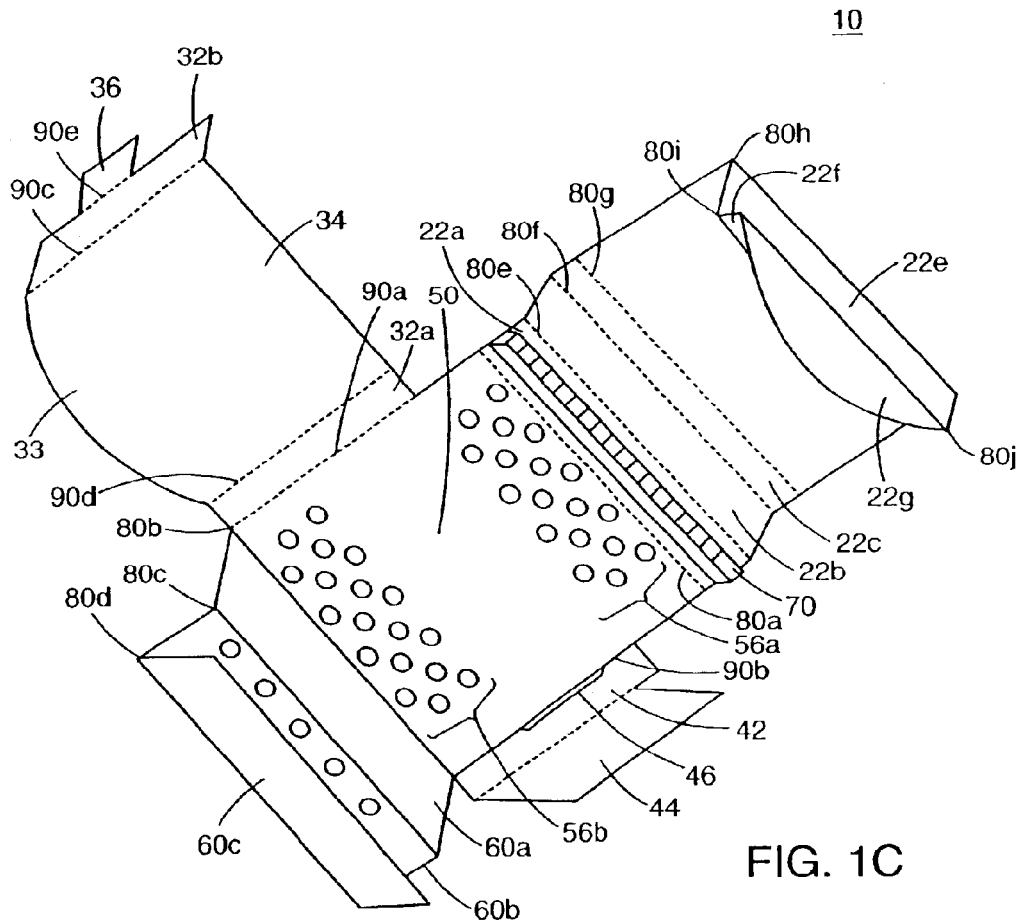
FIG. 1C is an isometric view of the package of FIG. 1A to further illustrate the fold lines.
Figure 1D:
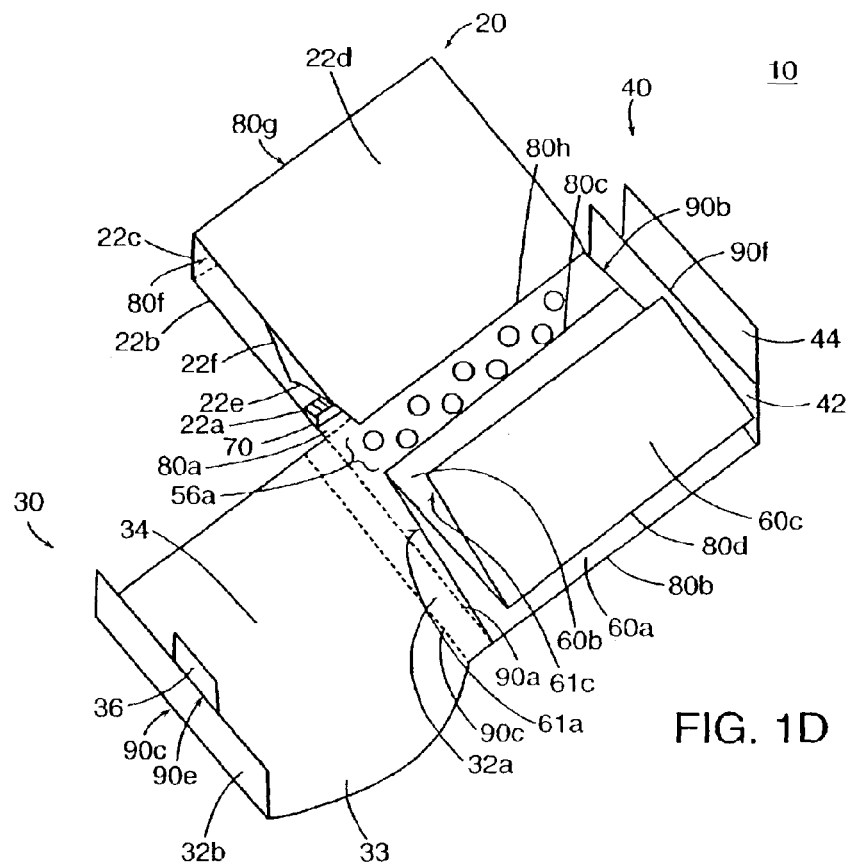
FIG. 1D is another isometric view of the package of FIG. 1A to illustrate certain elements of the folding of the package with the face cover member folded open for clarity.
Figure 1E:
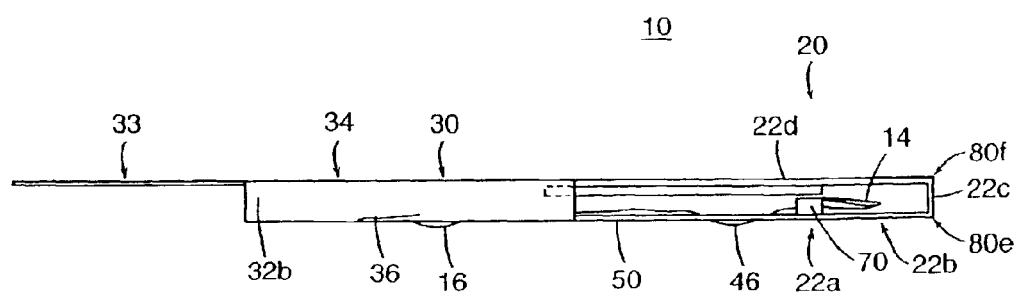
FIG. 1E is a side view of the package of FIG. 1B in the closed position.
Figure 2A:
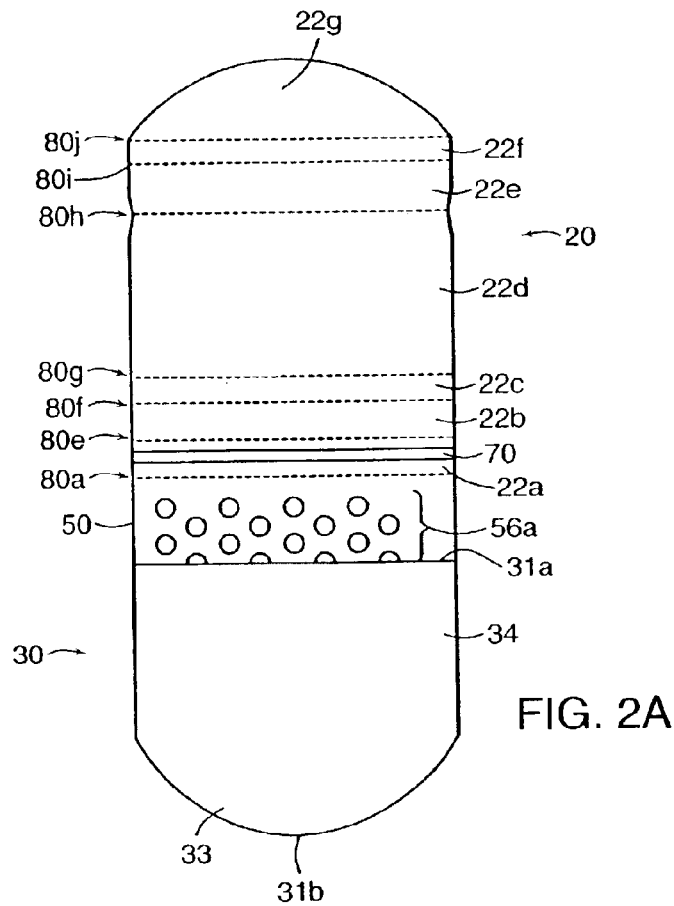
FIGS. 2A–C are diagrammatic views of the package of FIG. 1A illustrating the package folding process for forming a package handle.
Figure 2C:
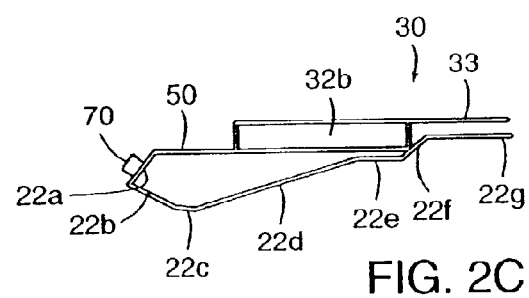
Figure 2B:
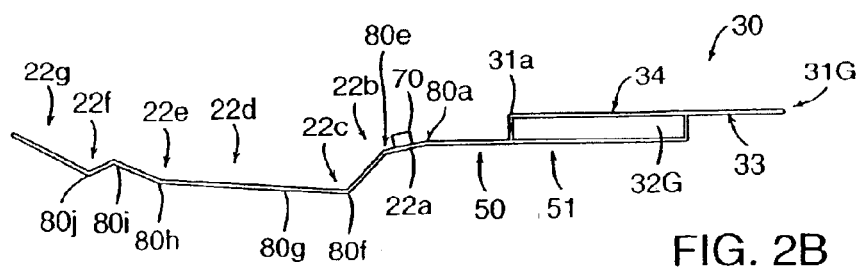
Figure 3A:
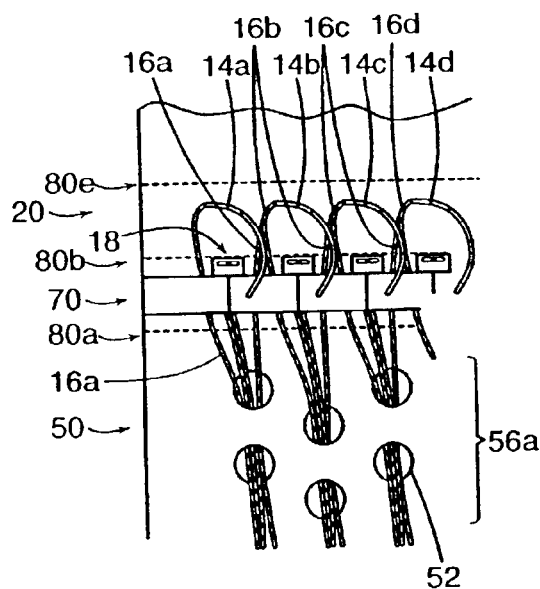
FIG. 3A is an exploded view of a portion proximal the left side of the package of FIG. 1B loaded with double-armed sutures in series.
Figure 3B:
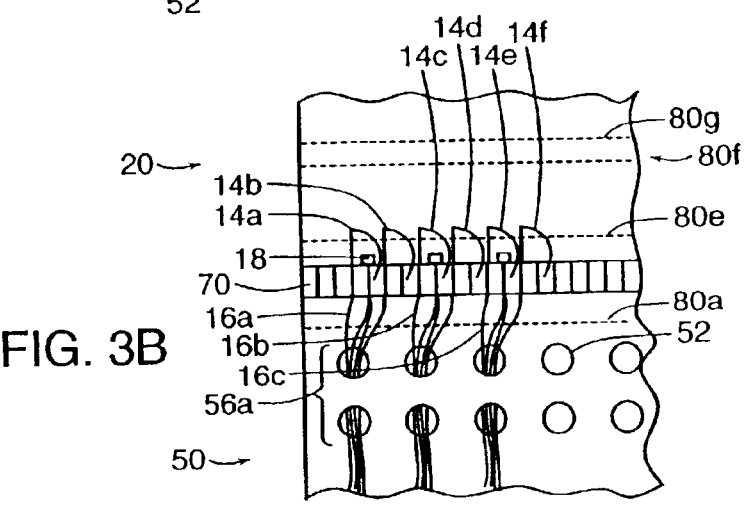
FIG. 3B is an exploded view of a portion proximal the left side of the package of FIG. 1A configured with in-line through aperture pairs and loaded with double-armed sutures that are not arranged in series.
Figure 3C:
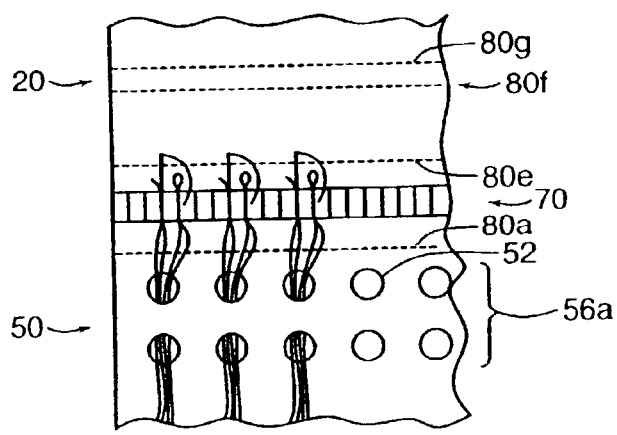
FIG. 3C is an exploded view of a portion proximal the left side of the package of FIG. 1A configured with in-line through aperture pairs and loaded with single-armed. sutures.

Referring now to the various figures of the drawing wherein like reference characters refer to like parts, there is shown in FIGS. 1–3 various views of one embodiment of a suture-needle or medical device package 10 according to the present invention. More specifically, there is shown in FIGS. 1A–E various views of the package 10 in the loaded and unloaded condition; FIGS. 2A–C generally illustrate the process to create a handle for this package 10 or any other any package of the present invention so the medical device therein can be easily grasped by the user for its withdrawal from the package; and FIGS. 3A–C illustrate more specific details as to the way specific suture-needle combinations or suture products are secured within this or other packages according to the present invention.

Now referring to FIGS. 1A–E, there is generally illustrated a package 10 that is particularly configured for storing therein at least one suture 16 with a needle 14 disposed at least at one end thereof. In the illustrated embodiment, each suture 16 being stored therein is provided with a needle 14 at both ends of the suture and with a pledget 18 attached to the suture and disposed between the suture ends. As indicated above, although these figures are illustrative of a package configured with a particularly suture-needle combination, this is not a limitation, as the package can be used or adopted for use with any medical device that is or can be interconnected to a flexible component including, but not limited to bundled ligatures (see also FIG. 6), double-stranded needles (see also FIG. 3A) double-armed sutures (see also FIG. 3B), single-stranded needles (see also FIG. 3C), looped sutures, braided steel, and other flexible medical components with accessory devices. Also generally included is any medical device including at least one rigid member and a flexible component interconnected thereto, for which easy access to the device and withdrawal from the package during a medical procedure is desirous.

The package 10 includes a generally flat unit 12 and a foam mounting strip 70 or needle retainer, that is disposed on the flat unit. The flat unit 12 is made from any of a number of materials known to those skilled in the art including paper products, and plastics. More particularly, the materials used to make the flat unit 12 can be any sheet material known in the art, including laminated paper products (e.g. box board, corrugated board), polymer sheeting or molded plastics, that has the rigidity and stiffness for the application and use, such as would be exhibited by the identified paper products. Paper products, such as solid box board, are preferable for the package because they are relatively inexpensive compared to other sheet materials, however, this preference shall not be construed as being a limitation. In an exemplary embodiment, the flat unit 12 of the package is formed from sulfate bleached stock.

The material comprising the flat unit 12 can be opaque, translucent, partially translucent, arranged with translucent windows or a combination thereof. Also, the paper product being used for the flat unit 12 may include a coating such as a wax or plastic coating or other coating material known in the box board/paper product art, which would be acceptable for such an application and which would not impede or otherwise have a negative effect on the withdrawal of the flexible component such as a suture 16 from the package 10.

The flat unit 12 is configured or arranged so as to include a handle panel or member 20, a face cover member 30, a cover securing member 40, a fixed or stationary panel 50, and a plurality of folding panels, more specifically, a first folding panel 60a, a second folding panel 60b and a third folding panel 60c. The flat unit 12 of the package 10 also is configured so as to include a plurality of fold lines. More particularly, a plurality of fold lines that are transverse to a long axis 11 of the flat unit 12, hereinafter transverse fold lines, and a plurality of fold lines that are parallel to the long axis, hereinafter side fold lines. These fold lines in conjunction with appropriately sized and arranged members and folding panels comprising the flat unit 12 allow the flat unit to be formed into a package or carrier that is compact for storage and use, in particular when compared to prior art packages, in particular those prior art packages used or intended for use in cardiovascular surgery.

The fixed or stationary panel 50 is generally defined by two exterior edges or sides 13b,d of the flat unit 12, a first transverse fold line 80a at one end thereof and a second transverse fold line 80b at an opposite end thereof. The first and second transverse fold lines 80a,b also extend across the width of the stationary panel 50. The stationary panel 50 also includes a plurality of through apertures 52 that are arranged in the stationary panel so as to form one or more columns of two rows, more particularly a first row 56a of through apertures and a second row 56b of through apertures.

The first and second rows 56a,b of through apertures 52 also are arranged so as to traverse the width of the stationary panel and so as to be transverse to the flat unit long axis 11. Additionally, each column of through apertures 52 is arranged so as to be generally parallel to the flat unit long axis 11 and thus generally perpendicular to the first and second transverse fold lines 80a,b.

The through apertures 52 are further arranged so each of the first and second rows 56a,b include at least one and preferably a plurality of pairs of through apertures. Also, and as shown in FIG. 3B, in one specific embodiment, the through apertures 52 are arranged so the centers of pairs of through apertures for each row are aligned with each other across the width of the stationary panel 50. In another specific embodiment, as shown in FIGS. 1A and 3A, the pairs of through apertures 52 are arranged such that the through aperture pairs are alternately staggered by column across the width of the stationary panel. In other words, the centers of the through apertures in the odd numbered columns are aligned with each other, the centers of the through apertures in the even numbered columns are aligned with each other but the centers of the odd numbered and even numbered columns are not aligned with each other.

The first folding panel 60a is generally defined by the flat unit exterior sides 13b,d, the second transverse fold line 80b and a third transverse fold line 80c and is pivotably or foldably connected to the stationary panel 50 by means of the second transverse fold line. Preferably the first folding panel 60a is configured so the top surface 61a thereof is relatively smooth and does not include any surface artifacts that could cause a suture 16 to hang up when it is being withdrawn from the package 10. As shown in FIG. 1D, when the first folding panel 60a is pivoted about the second transverse fold line 80b, the first folding panel top surface 61a is disposed generally over a portion of the stationary panel 50. In a particular embodiment, the first folding panel 60a is generally disposed over the portion of the stationary panel 50 including the second row 56b of through apertures 52.

The second folding panel 60b is generally defined by the flat unit exterior sides 13b,d, the third transverse fold line 80c and a fourth transverse fold line 80d. The second folding panel 60b also is pivotably or foldably connected to the first folding panel 60a by means of the third transverse fold line 80c. Similar to the stationary panel 50, the second folding panel 60b includes a plurality of through apertures 52 that are arranged so as to form one or more columns of the third row 56c of through apertures, more particularly another row of pairs of through apertures. Reference should be made to the foregoing discussion regarding the through apertures 52 provided in the stationary panel 50 for other details or features regarding the arrangement of the through apertures, such as the alignment of the through aperture centers. As shown in FIG. 1D, when the second folding panel 60b is pivoted about the third transverse fold line 80c, the bottom surface of the first folding panel 60a opposes the bottom surface of the second folding panel 60b.

The third folding panel 60c is generally defined by the fourth transverse fold line 80d, the flat unit exterior sides 13b,d and an exterior edge 13a of the flat unit 12. The third folding panel 60c also is pivotably or foldably connected to the second folding panel 60b by means of the fourth transverse foldline 80d. Preferably, the third folding panel 60c is configured so the top surface 61c thereof is relatively smooth and does not include any surface artifacts that could cause a suture to hang up when it is being withdrawn from the package 10. As shown in FIG. 1D, when the third folding panel 60c is pivoted about the fourth transverse fold line 80d, the top surface 61c thereof is disposed generally over the top surface of the second folding panel 60b. The third folding panel 60c generally assures that each suture 16 in the package 10 does not tangle and applies a gentle pressure against the suture in the assembled package.

FIGS. 1C and 1D are isometric views of the package 10 that generally illustrate how the various panels comprising the package, in particular the first through third folding panels 60a–c, are pivoted or folded about each of the transverse fold lines and the side fold lines as described herein to form a package 10 according to the present invention. FIG. 1D also is generally illustrative of how the top and bottom surfaces of the first and third folding panels 60a–c are arranged with respect to each other and the stationary panel 50, when these folding panels 60a–c are pivoted or folded about their respective transverse fold lines 80b–d. FIG. 1D, also is illustrative of the folding of the handle/cover member 20 when the package 10 is in its stored or closed condition.

Extending outwardly from the stationary panel 50 and generally transverse to the flat unit long axis 11 are the face cover member 30 and the cover securing member 40. The face cover member 30 is pivotably or foldably connected to the stationary panel 50 by means of a first side fold line 90a and the cover securing member 40 is pivotably or foldably connected to the stationary panel by means of a second side fold line 90b. The first and second side fold lines 90a,b are orientated so they generally extend parallel to the flat unit exterior sides 13a,b. In a more particular embodiment, the first and second side fold lines 90a,b are located so as to lie along the line formed by one of the respective flat unit exterior sides 13a,b.

The face cover member 30 includes two side panels 32a,b, a center panel 34 and a tab 36. Opposing sides of the first side panel 32a are generally defined by the first side fold line 90a and third side fold line 90c and the first side panel 32a is pivotably or foldably connected to the stationary panel 50 by the first side fold line 90a. The first and third side fold lines 90a,c, are spaced from each other a predetermined distance so the first side panel 32a has a width sufficient to accommodate the combined thickness of the first through third folding panels 60a–c, when they are folded back upon the stationary panel 50 as herein described.

The center panel 34 is generally defined by a top edge 31a, a bottom edge 31b, and the third and fourth side fold lines 90c,d, where the third side fold line 90c pivotably or foldably connects the first side panel 32a to the center panel and the fourth side fold line 90d pivotably or foldably connects the center panel to the second side panel 32b. The third and fourth side fold lines 90c,d are spaced from each other so that the center panel 34 has a width sufficient to at least extend across the width of the stationary panel 50.

Referring also to FIGS. 2A–C, the top edge 31a and the bottom edge 31b are spaced from each other so that the center panel has a length sufficient to at least extend along the flat unit long axis 11 so as to cover a significant portion of the stationary panel 50 and the folding panels 60a–c when they are folded back over the stationary panel. In a particular embodiment, the center panel length is set so the center panel 34 extends at least between second transverse fold line 80b and up to about the first row 56a of the through apertures 52 as illustrated in FIGS. 1D and 2A.

Preferably, the center panel 34 is configured so as to include an extension segment 33 and so that the bottom edge 31b extends outwardly from the second transverse fold line 80b when the package 10 is in its assembled or closed condition (e.g. see FIGS. 1E and 2B–C). This extension segment 33 is utilized in conjunction with the handle/cover member 20 to form a handle with which the user can hold onto the package 10 when the sutures are to be withdrawn therefrom. In an exemplary embodiment, the bottom edge 31b is preferably arcuate with a chord in line or aligned with the second transverse fold line 80b, although other shapes (e.g., linear, oblong, paddle shaped or rectilinear) are contemplated and thus within the scope of the present invention.

The flap or tab 36 is pivotably or foldably connected to the second side panel 32b by means of a fifth side fold line 90e. The tab 36 also is configured and sized so that it can be received in a tab securing slot 46 provided in the cover securing member 40. The width of the second side panel 32b also is preferably set so the tab 36 can be received in this slot 46 when the face cover member 30 is folded about the stationary panel 50. Additionally, the width of the second side panel 32b is preferably set so that, when the tab is so secured in the slot 46, the second side panel will have a width sufficient to accommodate the combined thickness of the first through third folding panels 60a–c when they are folded back upon the stationary panel 50 as herein described.

The cover securing member 40 includes a side panel 42, a top panel 44 and a tab securing slot 46 or aperture in which is received the face cover member tab 36. Preferably, the tab securing slot 46 is formed in a portion of the second side fold line 90b such that the slot extends along this fold line. This is not a limitation, however, as the tab securing slot 46 can be located in any portion of the securing member side panel 42 with a corresponding adjustment to the width of the face cover member second side panel 32b.

The securing member side panel 42 is pivotably or foldably connected to the stationary panel 50 by means of the second side fold line 90b. Similar to the face cover member first side panel 32a, the securing member side panel 42 is generally sized so has to have a width sufficient to accommodate the combined thickness of the first through third folding panels 60a–c, when they are folded upon the stationary panel 50 as herein described. The securing member top panel 44 is pivotably or foldably connected to the securing member side panel 42 by means of a sixth side fold line 90f. The securing member top panel 44 is sized and configured so that it is over a portion of the folded back first through third folding panels 60a–c and beneath the face cover member center panel 34 when the face cover member 30 is folded over the portion of the stationary panel 50.

The handle/cover member 20 extends outwardly from the stationary panel 50 along the first transverse fold line 80a and is pivotably or foldably connected to the stationary panel 50 by means of the first transverse fold line. The handle/cover member 20 also is generally defined by the flat unit exterior sides 13b,d, an arcuate edge 13c of the flat unit and the first transverse fold line 80a. The handle/cover member (HCM) 20 includes HCM first through HCM seventh panels 22a–g, and a multiplicity of transverse fold lines 80e–j that extend across the width of the handle/cover member.

The HCM panels 22a–g and the transverse fold lines 80e–j are sized and/or arranged so that in one case the handle/cover member 20 can be positioned in a closed position to form a cover over the exposed sutures 16 and needles 14 and in another case it can be re-positioned or reconfigured and used in conjunction with the face cover member extension segment 33 so as to form a package handle for the user when removing the sutures 16 from the package 10. The HCM panels 2a–g also are sized so the width of each generally equals the width of the stationary panel 50. The following describes the arrangement of the various HCM panels and transverse fold lines making up the handle/cover member 20.

The fifth transverse fold line 80e is spaced from the first transverse fold line 80a so the HCM first panel 22a has a length sufficient to receive the foam mounting strip 70. Additionally, the length for each of the stationary panel 50, the first and second folding panels 60a,b and a portion of the length for the HCM first panel 22a is set so as to have a combined length that can accommodate the desired length of the sutures 16 that extend to/from the foam mounting strip 70 and the through apertures 52 in the third row 56c as illustrated in FIG. 1B.

Figure 8A:
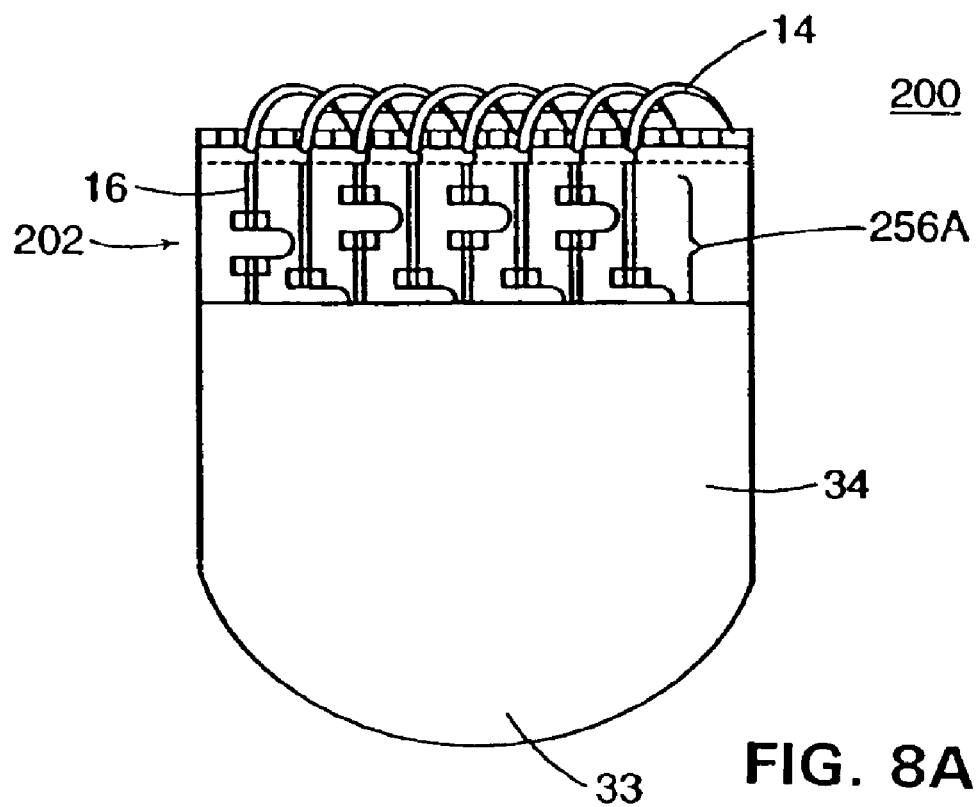
FIG. 8A is a diagrammatic front view of an illustrative package according to the present invention after the package handle is formed and the package is ready for withdrawal of sutures therefrom.
Figure 8B:
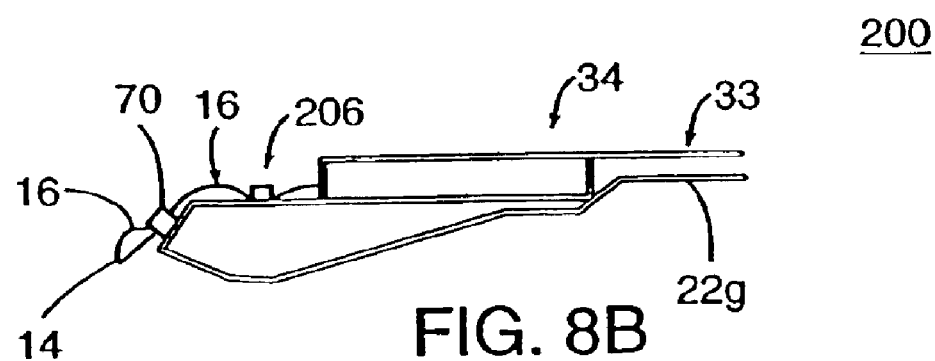
FIG. 8B is a diagrammatic side view of the package of FIG. 8A showing the presentation of the needles.

The length of the HCM first panel also is established so that a portion of each medical device or needle 14 and/or flexible component or suture 16 extends beyond the fifth transverse fold line 80e. In this way, this portion of each needle 14, for example, extends beyond the end or confines of the package when the handle/cover member 20 is folded back as shown in FIG. 2C to create the handle for the package. Such an arrangement advantageously presents the needles 14 to the user (e.g., scrub nurse or surgeon) so that each needle can be easily and successively removed from the package 10 without entangling the sutures 16 as well as the pledget 18 (see also FIG. 8B). In particular, such an arrangement presents the needles 14 so they can be easily loaded into a needle holder. Additionally, the presentation of the needles 14 in this fashion allows the user to withdraw them in either a left to right direction or right to left direction without entangling the sutures as they are being withdrawn from the package 10.

Additionally, the length of the HCM first panel 22a also is established such that when the handle/cover member 20 is being configured to form the package handle, the HCM first panel 22a is at an angle with respect to the top surface of the stationary panel 50 As illustrated in FIG. 2C, the HCM first panel 22a is angled backwardly from the top surface of the stationary panel 50 (i.e., angle between stationary panel top surface and HCM first panel top surface >180°). It is within the scope of the present invention, however, for the HCM first panel 22a to be substantially parallel to stationary panel top surface or at nearly any other orientation, when the package 10 is put into the open position.

The fifth and sixth transverse fold lines 80e,f are spaced from each other so the length of the HCM second panel 22b is such that the portions of the medical devices or needles 14, which project above the foam mounting strip 70, do not extend beyond the sixth transverse fold line 80f and thus are only disposed a relatively short distance over the HCM second panel. In this way, when the handle/cover member 20 is put into the closed position, the medical devices or needles 14 should not contact the HCM third panel 22c when it is pivoted or folded about the sixth transverse fold line as illustrated in FIG. 1E.

As indicated above, in the closed position, the handle/cover member 20 is positioned beneath the face cover member 30 so as to form a part of the cover that is formed over the sutures 16 and needles 14 being stored in the package 10. More particularly, the HCM third and fourth panels 22c,d are pivoted or folded, respectively, about the sixth and seventh transverse fold lines 80f,g such that the HCM third panel 22c forms a side of the package 10 and the HCM fourth panel 22d forms a portion of the top or cover for the package 10, the other portion of the top or cover being formed by the face cover member center panel 34 as illustrated in FIG. 1E. Additionally, the HCM fifth panel 22e is folded or pivoted about the eighth transverse fold line 80h so the HCM fifth through seventh panels 22e–g are generally disposed beneath the HCM fourth panel 22d as described further herein.

From such folding or pivoting about the sixth and seventh transverse fold lines 8f,g, the HCM third panel 22c is disposed at an angle with respect to the fixed panel top surface and the HCM fourth panel 22d is disposed at an angle with respect to a top surface of the HCM third panel. Also, such folding or pivoting preferably disposes a top surface of the HCM fourth panel 22d away from and above the top surface of the stationary panel 50 and the HCM first and second panel top surfaces so the HCM fourth panel 22d does not generally contact the sutures 16 and needles 14. In a particular embodiment, the HCM third panel 22c is generally perpendicular with respect to the HCM second panel top surface and the HCM fourth panel 22d is generally parallel to the stationary panel top surface.

To effect the described positioning of the HCM fourth panel 22d, the sixth and seventh transverse fold lines 80f,g are spaced from each other so the HCM third panel 22c has a length that is sufficient so that the HCM fourth panel 22d is so disposed above the stationary panel 50, the sutures 16, the needles 14 and the foam mounting strip 70 as illustrated in FIG. 1E. The seventh and eighth transverse fold lines 80g,h also are spaced from each other so the HCM fourth panel 22d has a length sufficient to extend along the flat unit long axis 11 so the edge formed by the eighth transverse fold line 80h can be inserted beneath and beyond the top edge 31a of the face cover member center panel 34. The length of the HCM fourth panel 22d also is established such that the edge formed by the eighth transverse fold line 80h can be later withdrawn by the user (e.g. surgeon, scrub nurse) from underneath the face cover member center panel 34 for purposes of creating the handle and for opening the package 10 so the medical devices or needles and/or flexible components or sutures can be withdrawn therefrom.

The sides of the HCM fourth and fifth panels 22d,e about the eighth transverse fold line 80h preferably are arranged or configured to locally reduce the width of these panels in the area proximal the edge formed by the eighth transverse fold line. This is done to make it easier to insert this edge of the HCM fourth and fifth panels 22d,e in the opening formed by the face cover member 30 and the cover securing member 40, in particular the face cover member center panel 34, the face cover member second side panel 37b and the covering securing member side panel 42. In an exemplary embodiment, a portion of each side of the HCM fourth and fifth panels 22d,e is sloped towards and about the eighth transverse fold line 80h, thus reducing the width of the HCM fourth and fifth panels proximal the eighth transverse fold line.

As indicated above, when the handle/cover member 20 is in the closed position, the HCM fifth through seventh panels 22e–g are generally disposed beneath the HCM fourth panel 22d. In one illustrative embodiment, as shown in FIG. 1E, the HCM fifth through seventh panels 22e–g are arranged to form a generally flat member that is disposed under the HCM fourth panel 22d. In a second illustrative embodiment, as shown in FIG. 1D, the HCM fifth through seventh panels are pivoted about the eighth through tenth transverse fold lines 80h–j so as to form a structure, for example a V shaped structure, that allows the HCM fourth panel 22d to deflect. In a third illustrative embodiment, the fifth through seventh panels 22e–g are further pivoted or folded about their respective transverse fold lines 80h–j so that the HCM sixth panel 22f extends between and is substantially perpendicular to the HCM second panel top surface. More specifically, when the HCM sixth panel 22f is so configured, it in effect acts like a wall internal to the package.

Referring now also to FIGS. 2A–C, when a user is to withdraw sutures, the handle/cover member 20 is withdrawn from underneath the face cover member 30 and the handle/cover member is unfolded from the "closed position" in preparation of forming the package handle. After the handle/cover member 20 is withdrawn, the user grasps the HCM sixth panel 22g and folds the handle/cover member 22 backwards behind the back surface 51 of the stationary panel 50 until the HCM sixth panel is proximal the face cover member extension segment 33, as shown in FIG. 2C. During this package handle forming process, the handle/cover member 20 pivots or folds about the first and fifth through tenth transverse fold lines 80a, 80e–j so as to automatically re-configure the handle/cover member and to present the needles 14 and sutures 16 for removal. Additionally, the handle/cover member 20 is arranged such that, when it is so re-configured to form the package handle, it does not compress or crush other parts of the package 10 that might restrict or impede withdrawal of the sutures 16 or flexible member therefrom. In an exemplary embodiment, the handle/cover member 20 is re-configured so as to be in the arrangement illustrated in FIG. 2C (see also FIG. 8B).

The handle created by the foregoing process is remote from the area of the package 10 in which the needles 14 and sutures 16 (i.e., medical device rigid and flexible members) are stored and it may be of nearly any shape or form. Such a handle yields a package configuration that eliminates the potential for crushing of or compressing the package that might inhibit or restrict the easy delivery or removal of the needles and sutures therein. This is particularly advantageous in comparison to prior art packages for storing sutures used in cardiovascular surgery, because the normal tendency of the user is to grasp these prior art packages in the center thereof This would pinch the package causing difficulties in removing the sutures from the prior art package.

It is within the scope of the present invention for the handle formed by this process for this package 10, or any other package of the present invention, to further include a handle extension. The handle extension preferably is a separate member not formed from the flat unit 12 that is secured to one or both of the HCM sixth panel 22g or the face cover member extension segment 33. The handle extension allows the package 10 to be located or positioned a distance away from the person holding the package, thus allowing the package to be more easily located proximal the medical or surgical field. The handle segment is generally configured to have sufficient rigidity to undesirable bending or deflection of the handle segment when the package 10 is being supported from one end thereof and being held by the user at the other end. In exemplary embodiments, the handle extension includes a flat wood member (e.g., tongue depressor), a tubular or rod member one end of which is flattened so as to be secured to the package or other structural configurations (e.g., I beams, channels) that are relatively resistant to such deflection or bending. The handle extension is secured to the HCM sixth panel 22g or the face cover member extension segment 33 using any of a number of techniques or means know to those in the art including adhesives. Additionally, a mechanism can be provided so as to generally secure the HCM sixth panel 22g and the face cover member extension segment 33 together when using the handle extension, such as for example by adhesives or a clip.

Referring to FIG. 1B there is shown a package 10 having a plurality of needles 14 and sutures 16 therein. The sutures 16 that are being loaded into the package, as indicated above, preferably are double-armed sutures, where a needle 14 is provided at each end of the suture. More particularly, and with reference also to FIG. 3A, there is shown a plurality of double-stranded needles or double-armed sutures that are arranged in series As also shown in FIG. 3A, for such a needle-suture combination or suture product, the first suture 16a extends between the first and second needles 14a,b; the second suture 16b extends between the second and third needles 14b,c; the third suture 16c extends between the third and fourth needles 14c,d and so forth to the n-1 suture, which extends between the n-1 needle and the $n^{th}$ needle. As also shown in FIGS. 1B and 3A, each suture is provided with a pledget 18 that is preferably disposed above the foam mounting member 70. It is within the scope of the present invention for the pledget 18 to be disposed below the foam mounting member 70.

As shown in FIGS. 1B and 3A, the point of the first needle 14a is inserted into the foam mounting strip 70 and a portion of the first suture 16a or suture strand is passed through a slit in the foam mounting strip 70. The suture or suture strand typically is longer than the distance between the foam mounting strip 70 and the third row 56c, thus, and as illustrated, the suture or suture strand is typically formed into one or more loops for loading. As such, a portion of the one or more loops for the first suture is passed through the slit in the foam mounting strip 70. In this way, one end for each of the one or more loops is releasably secured at the foam mounting strip 70.

Thereafter, the one or more loops of the first suture 16a is passed through the first through aperture 52 of the through aperture pair in the first row 56a of the first column, then along the back surface of the stationary panel 50 and then back up through the second through aperture of the pair. The one or more loops of the first suture 16a then pass along the top surface of the stationary panel 50 to the next through aperture pair in the second row 56b of the first column and then pass through this through aperture pair in a similar fashion to that described for the through aperture pair in the first row 56a.

The one or more loops of the first suture 16a then pass along the top surface of the stationary panel 50 and the top surface for each of the first and second folding panels 60a,b to the next through aperture pair in the third row 56c of the first column disposed in the second folding panel 60b. The one or more loops of the first suture 16a then pass down through the first through aperture of this pair, across a back surface of the second folding panel 60b and then up through the second through aperture of the pair so the end of the one or more loops are disposed on the second folding panel top surface 61b.

If the first suture 16a includes a pledget 18, then, the portion of the first suture containing the pledget, as illustrated more clearly in FIG. 3A, is disposed so the pledget remains above the foam mounting strip. In a preferred embodiment, the pledget 18 is arranged so as to be resting upon a side surface of the foam mounting strip 70. As indicated above, it also is within the scope of the present invention for the pledget 18 to be disposed below the foam mounting strip.

Although the foregoing essentially describes loading one or more loops of the suture or suture strand at the same time, this shall not be construed as a limitation. It is within the scope of the present invention for the suture or suture strand loops formed between the two needles to be loaded in any possible fashion including individually, all together or in groups. For example, the one or more loops of the suture between one needle and the pledget 18 are passed or routed as a group through the three rows 56a–c of through aperture pairs and the one or more loops of the suture between the pledget and the second needle are thereafter passed or routed as a group through the three rows 56a–c.

Thereafter the second needle 16b is inserted into the foam mounting strip and this loading process is repeated for the second suture 16b except that the second suture is successively passed through the through aperture pairs in the three rows; 56a–c in the second column. This process is repeated until each of the sutures comprising the set of double-armed sutures are disposed in the three rows 56b–c of through aperture pairs of each successive column and all the needles are secured in the foam mounting strip 70. After the package 10 has been loaded, it is folded as described herein to form the assembled package.

With such an arrangement, the sutures 16 can be withdrawn from an assembled package without the sutures becoming entangled during their removal therefrom. The mounting of the pedgets 18 above the foam mounting strip 70 provides additional measures for preventing catching and tangling. Also, by thus arranging the needles 14 and sutures 16, there is no specific removal orientation. Thus, the needles 14 and sutures 16 can be withdrawn from right to left of from left to right. The foregoing also applies to sutures 16 or suture strands that are not arranged with a pledget 18.

As indicated above, a package according to the present invention is not limited to a suture product comprising double-stranded needle application, but also includes other suture products, for example, single stranded needles, looped sutures and doubled-armed sutures. There is shown in FIG. 3B a package in which is stored a plurality or more of double-armed sutures, including a pledget 18 for each suture. For such a suture product, the first suture 16a extends between the first and second needles 14a,b;the second suture 16b extends between the third and fourth needles 15c,d; the third suture 16c extends between the fifth and sixth needles 14e,f and so forth. Each of the double-armed suture are secured in the package 10 in a similar manner to that described above for the double stranded needles of FIG. 3A.

There also is shown in FIG. 3C, a package in which is stored a plurality or more of single stranded needles, a suture product where a needle is secured to one end of the suture and the other end of the suture is free or bare. In the illustrated embodiment, each needle 14 is secured in the foam mounting strip 70. As noted above the length of the suture 16 typically is longer than the distance between the foam mounting strip 70 and the third row 56c of through aperture pairs in the second folding panel 60b. As such to secure the suture 16 to the package, the free end of the suture and the needle 14 are located proximal to each other and portions of the two strands from the free end and the needle are both passed through one of the slits in the foam mounting strip 70.

As indicated above, when the suture 16 is longer than the distance between the mounting strip 70 and the third row 56c, the suture typically is arranged so as to form one or more loops. In such a case a portion of each loop is passed through one of the mounting strip slits so as to releasably secure one end of each of the one or more loops at the foam mounting strip 70. Thereafter, the one or more loops of the suture are successively passed through the three rows 56a–c of through aperture pairs for the first column as described above for the looped sutures for the double-stranded needles. The above is repeated for each single stranded needle being secured in the package in the three rows 56a–c of through aperture pairs of each successive column.

As also noted above, the one or more loops can be passed or routed through the three rows 56a–c of through aperture pairs in any possible fashion including individually, all together and in groups. It also is within the scope of the present invention, for the free end of the flexible component for a single stranded device or the suture for a single stranded needle to be successively passed back and forth through the three rows 56a–c of through aperture pairs and the slit(s) in the foam mounting strip 70 until the free end is proximally disposed above or below the foam mounting strip.

It should be recognized that the foregoing is not exhaustive of every possible suture product known in the art nor is it exhaustive of every possible length for a suture and the like. Thus, it is within the scope of the present invention to adapt the invention to retain other suture products within the package without departing from the scope and spirit of the invention disclosed herein. Additionally, it is within the scope of the present invention for a suture strand or the one or more loops of a suture strand to be passed successively through the rows of through aperture pairs in a given column as many times as required dependent upon the length of the suture strand and the configuration of the package.

In the foregoing three folding panels 60a–c and three rows 56a–c of through aperture pairs are illustrated and described, however, this shall not be construed as a limitation. The package 10 of the present invention can be adapted so as to include a multiplicity (i.e., four or more) of folding panels and more than three rows of through aperture pairs so as to accommodate the desired length of a suture. In this way, a package can be configured with additional folding panels and row(s) of through aperture pairs so as to be capable of releasably retaining a longer length suture while generally maintaining overall the compact size and configuration of a package for a shorter length suture. Thus, the handling of a package during a surgical procedure does not have to be altered or varied because of the length of the suture.

This package 10 or any other package according to the present invention is adaptable to include one or more additional folding panels extending generally outwardly from the third folding panel 60c. In a preferred embodiment, one or more pairs of folding panels are added to the package 10. In this case, one of the panels of each pair is configured so as to include an additional row of at least one through aperture pair like the second folding panel 60b and the other panel of each pair is configured like the third folding panel 60c without through aperture pairs. For example, a package can be configured with five folding panels and four rows of at least one through aperture pair, where the fourth row is disposed in the fourth folding panel.

The sutures 16 referred to herein are made of, for example, a non-absorbable polyester including braided polyester fibers, braided polyester fibers with a coating of polytetra-floroethylene (PTFE) (Polydek.RTM and Tevdek.RTM), polypropylene monofilament (Deklene RTM), silk, nylon, steel, or an absorbable material such as PGA. The pledgets 18 are formed from a variety of materials, for example felted PTFE, and are formed so as to have rectangular, square, oval, circular or other shape with a pair of openings through which a single suture strand passes. The needles 14 are constructed from any material known to those skilled in the art, including various alloys of stainless steel such as 300 series or 400 series stainless steel.

In a preferred embodiment, there is a plurality of different color sutures or suture strands that are alternately or sequentially provided in a set or series of double-stranded sutures. In particular embodiments, the suture colors include green, white and a co-braided green and white. When a two color scheme is used the colors would repetitively alternate back and forth in the series, for example, a green suture would extend between the first and second needles and a white suture would extend between the second and third needles and so forth. When a three color scheme is used the colors would alternate in sets of three sutures, for example, a green suture would extend between the first and second needles, a white suture would extend between the second and third needles and a co-braided green/white suture would extend between the third and fourth needles. Thereafter, the previous suture color pattern can be repeated or a different three color scheme (e.g., white, co-braided, and green) can be used for the next three sutures. It also is within the scope of the present invention for any suture product, including any of the above-illustrated suture products of FIGS. 3A–C to include sutures of different colors and different color combinations such as those described above. For example, the color of the suture for a single-stranded needle would be alternated by column.

Reference also should be made to co-pending application Ser. No. 09/360,709 (filing date of Jul. 26, 1999), the teachings of which are incorporated herein by reference, for further details regarding such sutures and needles, in particular double-armed sutures or double stranded needles.

The foam mounting strip 70 is a generally rectilinear member in cross section and has a length sufficient to carry the needles 14 and sutures 16 being stored in the package 10. This is not a limitation as other geometric configurations and lengths are contemplated and thus are within the scope of the parent invention. In an exemplary embodiment, the length of the foam mounting strip 70 is substantially equal to the width of the stationary panel 50. The foam mounting strip 70 also is constructed of a material known to have good sterility characteristics and that can releasably retain and protect the tip of the needle 14 therein. Additionally, the foam mounting strip 70 is configured with a plurality, preferably a multiplicity, of slits therein that extend across a top surface of the foam mounting strip in which can be received portions of the sutures 16 or flexible member.

In an exemplary embodiment, the foam mounting strip 70 is made from a plastic material such as polyethylene foam.

It is within the scope of the present invention, however, for the mounting strip 70 to be made from any of a number of materials known to those skilled in the art. The foam mounting strip 70 is secured to the HCM first panel 22a using any of a number of conventional techniques known to those skilled in the art including adhesives. Alternatively, the needles 14 or other medical devices can be secured to holding areas provided in or cut into portions of the HCM first panel 22a.

Alternatively, needle slots or a small amount of a non-reactive adhesive is applied to the top surface of the HCM first panel 22a in and about an area whereat the mounting strip 70 would be located. In this example, the needle 14, portions of the suture 16 and/or other medical device is releasably secured to the HCM first panel top surface by means of these slots or non-reactive adhesive. When the package is opened, the user releases the needle and suture from the slots or adhesive by pulling on the needle/suture product.

In the foregoing, a single foam mounting strip is described as being provided on the HCM first panel 22a, however, this shall not be construed as a limitation. It is within the scope of the present invention for a plurality or more of foam mounting strips to be disposed on the HCM first panel 22a. For example, two foam mounting strips can be provided on the HCM first panel 22a that are spaced from each other. With such an arrangement, the needles 14 can be alternately inserted into the two mounting strips so the odd numbered needles are inserted into one strip and the even numbered needles into the other strip. Similarly, the HCM first panel 22a can be configured with a plurality of rows of needle slots or areas on which is applied the non-reactive adhesive so as to have a similar effect.

Figure 4A:
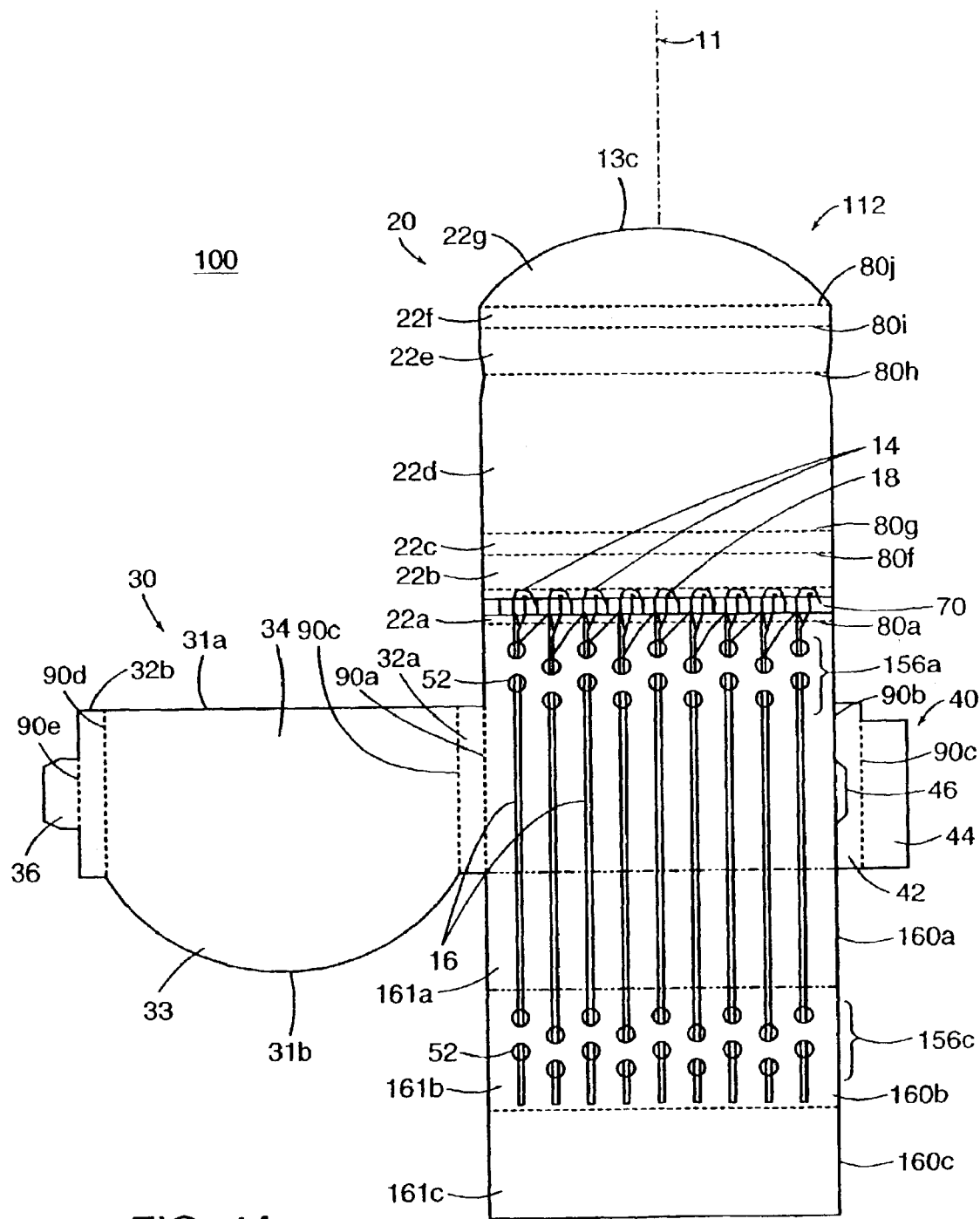
FIG. 4A is a plan view of a second embodiment of a package according to the present invention.
Figure 4B:
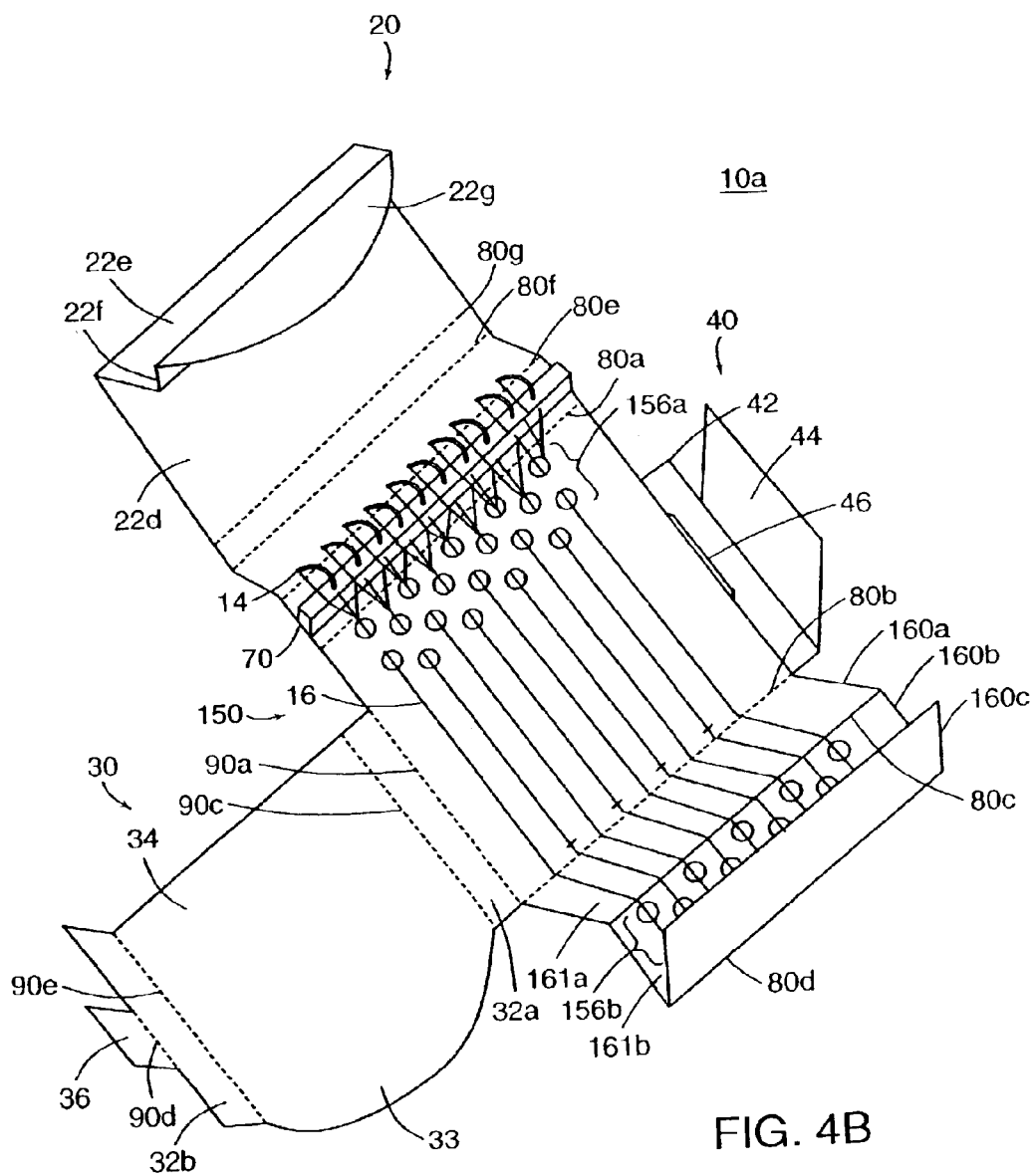
FIG. 4B is an isometric view of the package of FIG. 4A to further illustrate the fold lines.

There is shown in FIGS. 4A–B, a second embodiment of a package 100 according to the present invention. This package 100, as with the first embodiment, includes a generally flat unit 112 that is configured so as to have a handle/cover member 20, a face cover member 30, a cover securing member 40, a stationary panel 150, and first through third folding panels 160a–c. This flat unit 112 also includes a multiplicity of transverse fold lines, first through tenth transverse fold lines 80a–j and a multiplicity of side fold lines, first through sixth side fold lines 90a–f. The stationary panel 150 is configured so as to include a first row 156a of pairs of through apertures 52 or through aperture pairs and the second folding panel 160b is configured with a second row 156b of through aperture pairs.

The suture product illustrated in FIGS. 4A–B, is a double-stranded needle product in which double-armed sutures are arranged in series. As with the first embodiment, however, this package 100 can be used with any of the suture products described herein or known to those skilled in the art as well as medical devices that are or can be configured with an interconnecting flexible member.

As also shown in FIGS. 4A–B, the point of the first needle 14a is inserted into the foam mounting strip 70 and a portion of the first suture 16a or suture strand is passed through a slit in the foam mounting strip 70. The suture or suture strand typically is longer than the distance between the foam mounting strip 70 and the second row 156b, thus and as illustrated, the suture or suture strand is typically formed into one or more loops for loading. As such, a portion of the one or more loops for the first suture is passed through the slit in the foam mounting strip. In this way, one end for each of the one or more loops is releasably secured at the foam mounting strip 70.

Thereafter, the one or more loops of the first suture 16a is passed through the first through aperture 52 of the through aperture pair in the first row 156a of the first column, then along the back surface of the stationary panel 150 and then back up through the second through aperture of the pair. The one or more loops of the first suture 16a then pass along the top surface of the stationary panel 150, along the top surface 161a–b for each of the first and second folding panels 160a,b to the next through aperture pair in the second row 156b of the first column disposed in the second folding panel 160b. The one or more loops of the first suture 16a then pass through this through aperture pair in a similar fashion to that described for the pair of through apertures in the first row 156a. Preferably the other end for each of the one or more loops remain upon the second folding panel top surface 161b and do not extend onto the top surface 161c of the third folding panel 160c.

If the first suture 16a includes a pledget 18, then the portion of the first suture containing the pledget, as illustrated in FIG. 3A, is disposed within the package so the pledget remains above the foam mounting strip. In a preferred embodiment, the pledget 18 is arranged so as to be resting upon a side surface of the foam mounting strip 70. As indicated above, it also is within the scope of the present invention for the pledget 18 to be disposed below the foam mounting strip 70 and above the first row 256a of securing mechanisms 202.

Although the foregoing essentially describes loading one or more loops of the suture or suture strand at the same time, this shall not be construed as a limitation. It is within the scope of the present invention for the suture or suture strand extending between two needles to be loaded in any possible fashion including individually, all together, or in groups. For example, the one or more loops of the suture between one needle and the pledget are passed or routed as a group through the two rows 156a–b of through aperture pairs and the one or more loops of the suture between the pledget and the second needle are thereafter passed or routed as a group through the two rows 156a–b.

Thereafter, the second needle 16b is inserted into the foam mounting strip and the process is repeated for the second suture 16b except that the second suture is successively passed through the through aperture pairs in the two rows 156a–b of through aperture pairs in the second column. This process is repeated until each of the sutures comprising the set of double-armed sutures are disposed in the two rows 156a–b of through aperture pairs of each successive column and all the needles secured in the foam mounting strip 70. After the package 100 has been loaded, it is folded as described herein to form the assembled package.

Reference shall be made to the foregoing discussion for the package 10 of the first embodiment as to the details concerning the manner in which the various panels 150, 160 and members 20, 30, 40 of this package 100 are folded so as to put the package 100 in a closed or open condition as well as to form the handle. Reference also should be made to the foregoing discussion concerning the first embodiment as to details regarding materials of use and structural arrangement as well as other details of the structural elements in common with the first embodiment that are not otherwise described here.

Figure 5:
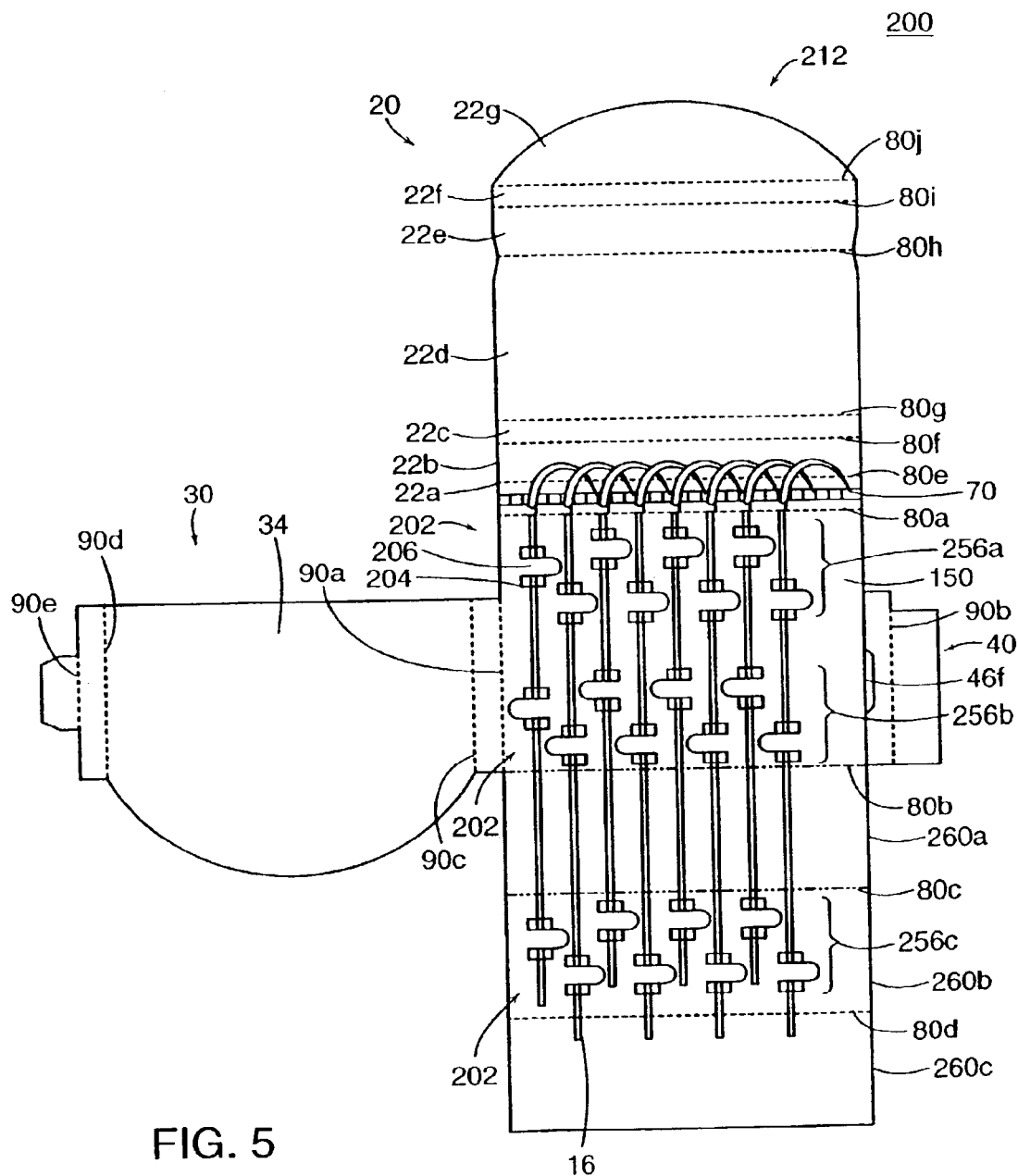
FIG. 5 is a plan view of a third embodiment of a package according to the present invention.

There is shown in FIG. 5 a third embodiment of a package 200 according to the present invention. This package 200 includes a generally flat unit 212 that is configured so as to have a handle/cover member 20, a face cover member 30, a cover securing member 40, a stationary panel 250, and first through third folding panels 260a–c. The flat unit 212 also includes a multiplicity of transverse fold lines, first through tenth transverse fold lines 80a–j and a multiplicity of side fold lines, first through sixth side fold lines 90a–f. Reference should be made to the foregoing discussion regarding the first and second embodiments for further details regarding the flat unit 212, the handle/cover member 20, the face cover member 30 and the cover securing member 40.

The stationary panel 250, and each of the first, second and third folding panels 260a–c are similar in most respects to the stationary panel 50, 150 and first through third folding panels 60a–c, 160a–c described in connection with the first and second embodiments. In the third embodiment, the stationary panel 250 and the second folding panel 260b are configured with a plurality of securing mechanisms 202 that locally secure the sutures or flexible members/components of a medical device to each of the stationary panel and the second folding panel and which securing mechanisms differ from that described above for the first and second embodiment. As such, reference should be made to the foregoing discussion for the equivalent components for other aspects and details of the fixed and folding panels 250, 260a–c.

There is provided in the stationary panel 250 at least one row of at least one securing mechanism and another row of at least one securing mechanism is provided in the second folding panel 260b. Preferably, the stationary panel 250 includes two rows, a first row 256a and a second row 256b, each row having at least one securing mechanism 202 and a third row 256c of at least one securing mechanism is disposed in the second folding panel 260b. Preferably, each securing mechanism 202 comprises a through aperture 204 and a tab 206 that is disposed over a center portion of the through aperture.

The tab 206 for each securing mechanism 202 is preferably positioned so that it is at the midpoint of the through aperture 204 and the through aperture is configured so that a portion of the through aperture complements the shape of the tab. Alternatively, the tab 206 is formed so that it overlays a portion of top surface of the stationary panel 250 and/or the second folding panel 260b proximal the through aperture.

In an illustrative embodiment, one side of the tab 206 is integral with the flat unit 212 so the tab 206 is pivotable about the juncture with the flat unit 212. Additionally, when forming such a tab, two through holes or openings 204a,b are formed on either side of the tab 206. These through holes or openings thus form the through aperture 204.

In a preferred embodiment, each of the three rows 256a–c includes a plurality of securing mechanism 202 that are formed or arranged in the stationary panel 250 and the second folding panel 260b so as to form one or more columns of rows of securing mechanisms. In particular, the through apertures 204 for each securing mechanism 202 are arranged or formed so the through apertures form three rows of through apertures of one or more columns. Additionally, the through aperture 204 of each securing mechanism 202 in each row 256a–c is arranged such that the centers of the through apertures or the tabs 206 therefor for each column are aligned with each other(see for example FIG. 3B), or as shown in FIG. 5, the through apertures in a given row are alternately staggered by column across the width of the stationary panel 250 and/or the second folding panel 260b.

Although three rows 256a–c of securing mechanisms 202, or through apertures 204 and corresponding tabs 206, in a plurality of columns is shown in FIG. 5 this is not a limitation. The package 200 according to the third embodiment also can be configured so as to include two rows of the securing mechanisms 202 (e.g., apertures 204 and tabs 206), one row disposed in the stationary panel 250 and a second row in the second folding panel 260b as similarly illustrated in FIGS. 4A,B. Additionally, and as with the first and second embodiments, this package 200 also can: be configured so as to have a multiplicity (i.e., four or more) of folding panels and four or more rows of securing mechanisms 202 (e.g. apertures 204 and tabs 206). Reference should be made to the foregoing discussion regarding the first and second embodiments for further details of these features.

When a suture product is to be locally and removably secured within the package 200, the first needle 14a is inserted into the foam mounting strip and the suture or the one or more loops comprising the suture is passed beneath the tab 206 comprising the securing mechanism 202 in the first row 256a. This can be accomplished, for example, by sliding the suture or the one or more loops under the tab 206, for example, by lifting the tab upwardly. Alternatively, this can be accomplished by passing the suture or the one or more loops through the through hole or opening 204a on one side of the tab 206, then under the tab and then up through the through hole 204b on the other side of the tab. The suture or the one or more loops also are thus secured to the securing mechanisms 202 in each of the secondhand third rows 256b,c comprising a column in the described fashion (i.e. passed beneath the tab) so the suture is releasably secured to the package 200. As indicated above, the pledget 18 is preferable disposed above the foam mounting strip 70, however, it is within the scope of the present invention to secure the pledget below the mounting strip and above the first row 256a of securing mechanisms 202.

After securing the first suture in the package 200, a second needle 14b is inserted into the foam mounting strip and the process is repeated for the next suture except that the next suture is successively secured to the securing mechanisms 202 in the three rows 256a–c in the second column. This process is repeated until each of the sutures comprising the set of double-armed sutures are disposed in the three rows 256a–c of securing mechanisms 202 of each successive column and the needles secured in the foam mounting strip 70. After the package 200 has been loaded, it is folded as described herein to form the assembled package.

Reference should be made to the foregoing discussion regarding the first and second embodiments concerning other aspects of the routing of the suture or the one or more loops comprising the suture, such as for example, the insertion of needles 14 into the foam mounting strip 70 and the different ways in which the suture or one or more loops can be routed through the securing mechanisms 202 (e.g., individually, in groups) as well as for the different types of suture products.

Figure 6:
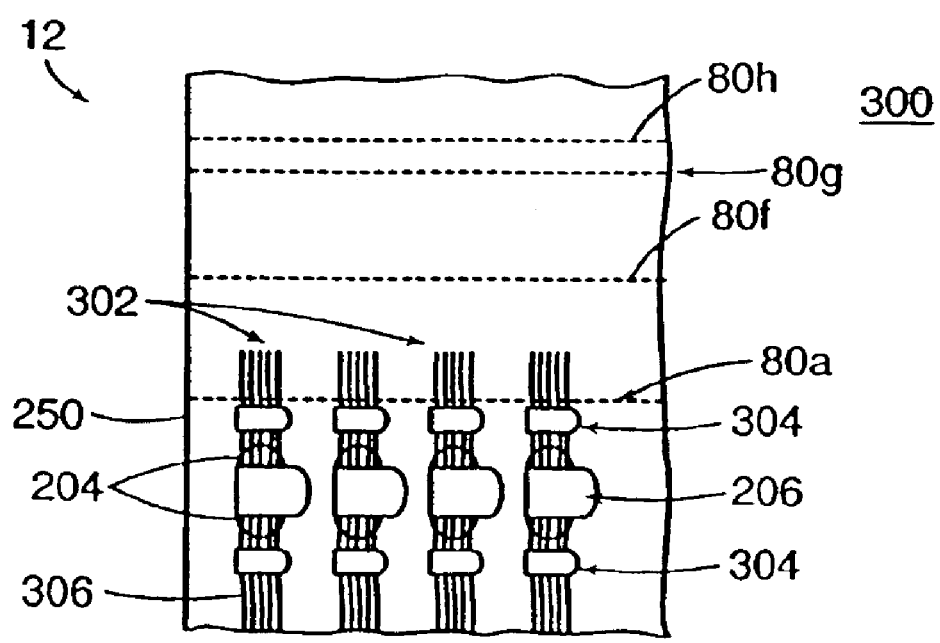
FIG. 6 is an exploded view of a portion proximal the left side of a package according to a fourth embodiment.

As provided above, a package according to the present invention is not limited for use with just suture products, but rather the package can be adapted for use as a means to releasably retain any of a number of medical devices including at least one rigid member that is interconnected to a flexible member. There is shown in FIG. 6, a fourth embodiment of a package 300 according to the present invention that is illustrative of such other medical device use. The package 300 shown in FIG. 6 is particularly configured for storing bundled ligatures 302 that each include a pair of clips 304 and a plurality of flexible members 306. Typically, bundled ligatures are configured to include one or more clips 304. With reference also to FIG. 5, this package 300 includes a flat unit 212 having a handle/cover member 20, a face cover member 30, a cover securing member 40, a stationary panel 250 and first through third folding panels 260a–c. Also included is a plurality of transverse fold lines, first through tenth transverse fold lines 80a–j and a plurality of side fold lines, first through sixth side fold lines 90a–f. Reference should be made to the foregoing discussion regarding the first through third embodiments for details regarding these components, materials and the fold lines and the folding process for establishing a package that are not otherwise discussed here.

When a bundled ligature 302 is to be removably secured within the package 300, the flexible members 306 between a pair of clips 304 are slide under the moveable tab 206 of the securing mechanism 202 in the first row 256a of the first column, so that the clips are disposed on either side of the tab. The flexible members 306 are then successively slide under the tabs 206 of the securing mechanisms 202 in each of the second and third rows 156b,c of the first column.

After securing the flexible member 306 of the first bundled ligature 302 to the securing mechanism 202 in the three rows 256a–c of the first column of the package 300, the above process is repeated for the next bundled ligature except that the flexible members 306 of the next bundled ligature are secured to the securing mechanisms 202 in the three rows 256a–c in the second column. This process is repeated until all of the bundled ligatures 302 are secured in the three rows 256a–c of securing mechanisms 202 of each successive column. After the package 300 has been loaded, it is folded as described herein to form the assembled package.

In a preferred embodiment, the flat unit 12,112,212 of any of the above-described packages 10,100,200,300 is manufactured from a paper product, such as box board, using a conventional die cutting technique or any other equivalent technique known in the boxboard/paper product art. For the die cutting technique, the die being made is particularly configured to produce the product to be manufactured using any of a number of techniques known to those in the boxboard/paper product industry. The configured die is pressed onto a flat sheet of the paper product yielding a flat unit having the desired configuration and attributes. The pressing process is repeated until the required number of flat units is produced. Typically, a continuous length of the paper product is introduced into the pressing section to repetitively form the desired product.

For a flat unit for a package according to the present invention, the die is configured to cut the paper product to yield a flat unit including a handle/cover member, a face cover member, cover securing member, stationary panel, and the first through third folding panels, as well as any additional folding panels, as hereinabove described. The die also is configured so as to form the desired type of fold lines (e.g., scored or perforated type) for the transverse fold lines 80a–j and side fold lines 90a–f. Additionally, the die is configured to cut the paper product so as to yield the desired means for locally securing a suture or flexible member to the package such as the rows of through aperture pairs or the rows of securing mechanisms, each comprising an aperture and a tab. In more specific embodiments, the die is configured so as to produce any of the flat units illustrated in FIGS. 1–5.

The manner or method of making the transverse and side fold lines 80,90 is that known in the art for the sheet material being used. For example, for paper products the transverse and side fold lines 80,90 can be the scored type and/or perforated type. In an exemplary illustrative embodiment, the second and third transverse fold lines 80b,c are scored type of fold lines and the remaining transverse fold lines 80a, 80d–j and the side fold lines 90a–f are perforated fold lines.

After forming the flat unit, the foam mounting strip 70 is secured to the top surface of the HCM first panel 22a using any of a number of conventional techniques known to those skilled in the art as further described above. Alternatively, a small amount of a non-reactive adhesive is applied to the HCM first panel top surface generally in an area about the location of the foam mounting strip. Reference also should be made to the foregoing discussion for additional details regarding the other mechanisms or methods for forming a means to releasably secure the needle 14 and portion of the suture 16, as well as a medical device including a rigid member interconnected to a flexible member, to the package.

There is shown in FIGS. 7A–D diagrammatic views of a package 400 according to the present invention particularly configured for retaining suture products therein, that generally illustrate the process by which a package according to any aspect of the present invention is assembled for later use during a surgical or medical procedure. Although the package according to the third embodiment is illustrated, this is exemplary, as it is within the scope of the present invention for any of the above-described packages or carriers to be assembled in the following manner. Reference, shall be made to FIGS. 1–6 for any features not specifically shown in FIGS. 7A–D or described here.

As with the above-described packages, the package 400 shown in FIGS. 7A–D includes a handle/cover member 420, a face cover member 430, a cover securing member 440, a stationary panel 450, first through third folding panels 460a–c, transverse fold lines 480a–j, side fold lines 490a–f and a securing mechanism 402 to locally secure portions of flexible component such as a suture to the package. For purpose of clarity in the discussion of these figures, all features of the package are uniquely numbered even though they are common to that described above. Thus, reference shall be made to the foregoing discussion of the first through third embodiments for further details of the corresponding features referred to in the following.

Before the sutures 16 and needles 14 are mounted, the flat unit 412 is typically pre-folded along a number of the transverse and side fold lines to facilitate the later folding of the package 400 into the assembled or closed position or condition. After any such pre-folding, the flat unit 412, is generally returned to a flat state for purposes of mounting the sutures and needles. It is likely that the certain portions of the flat unit 412 after pre-folding will not be truly flat, however, this is within the meaning of being in a generally flat state.

The sutures 16 and needles 14 are secured to the foam mounting strip 470 and locally secured to one of the securing mechanisms 402 in each of the three rows 456a–c for locally securing the sutures to the stationary panel 450 and the second folding panel 460b. Reference should be made to the discussion above regarding FIGS. 1B, 4A–B and 5 as to the specific methodology for locally securing the sutures, for example lacing the suture through the pair of through apertures 52 in each row as shown in FIG. 1B or the use of a non-reactive adhesive in lieu of the foam mounting strip 70. As indicated above, the sutures 16 being removably secured are illustratively a plurality of double-armed sutures or double-stranded needles, having a needle at each end of the suture, and an pledget 18 disposed therebetween.

Additionally, these sutures are preferably in a color sequence so as to differentiate between adjoining sutures. For example, the sutures and needles could be arranged, for example, such that the even numbered and the odd numbered sutures are differently colored. Thus, when mounting the sutures to the foam mounting strip and the securing mechanism 402, care should be taken not to interweave the different colored sutures to avoid entanglement when withdrawing the suture. Other color suture schemes including those described above are within the scope of the present invention.

Figure 7A:
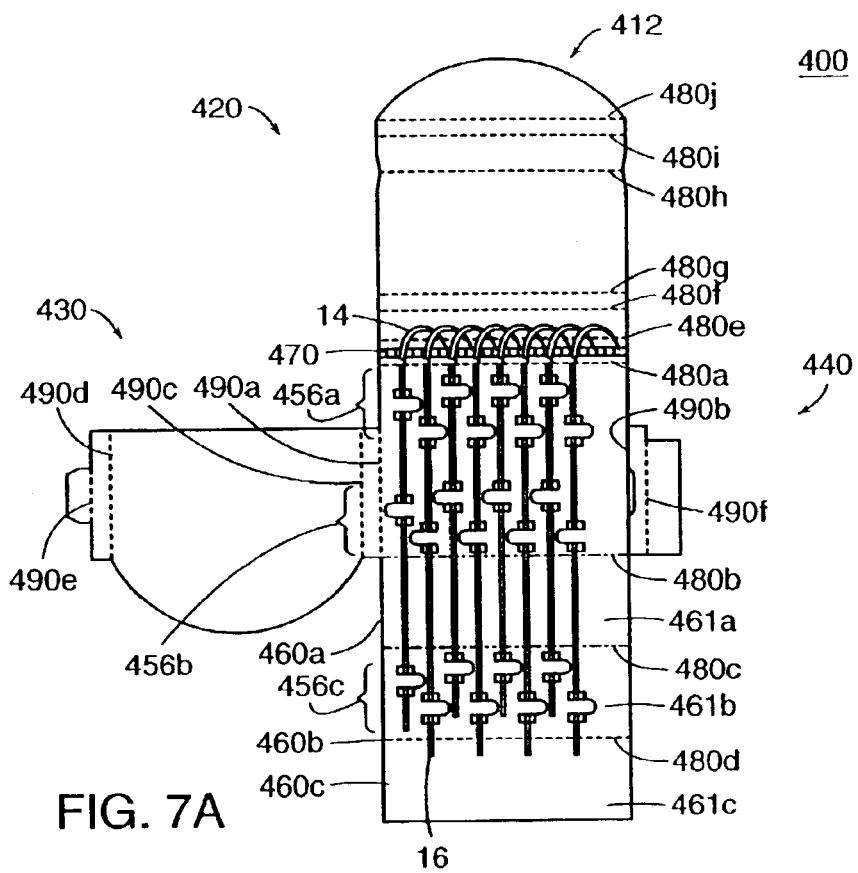
FIGS. 7A–D are diagrammatic views of an exemplary package according to the present invention illustrating folding such a package.
Figure 7B:
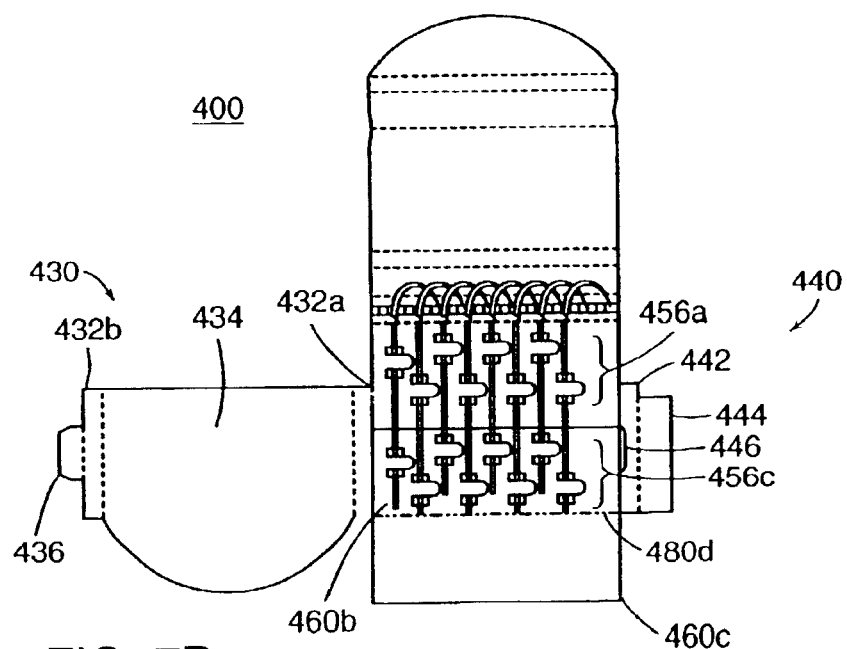
Figure 7C:
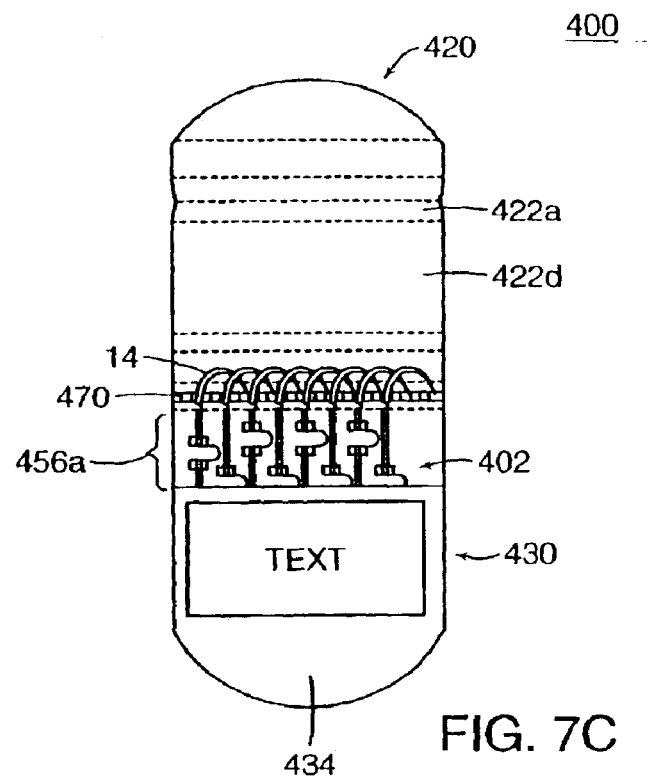

The mounting of each suture 16 and needle 14 to the package is repeated until all of the sutures and needles comprising the series, set or all of the sutures and needles to be secured thereto have been mounted thereon. An example of such a package 400 that is ready for folding into the final assembled package is shown in FIG. 7A.

After loading the sutures and needles, the first folding panel 460a is pivoted or folded about the second transverse fold line 480b upwardly so the top surface 461a of the first folding panel and the sutures lying thereon are disposed over a lower portion of the stationary panel 450, the portion including the second row 456b of the securing mechanisms 402. Preferably, the second folding panel 460b is concurrently folded downwardly about the third transverse fold line 480c so the bottom surface of the second folding panel is over the bottom surface of the first folding panel 460a. However, it is within the scope of the present invention for these steps to be performed sequentially. After so folding the first and second folding panels 460a,b, the ends of the sutures on the second folding panel are adjusted by gently pulling down on the sutures. The foregoing leaves a package 400 such as that shown in FIG. 7B, which is ready for further folding into the final assembled package.

In a more specific embodiment of the assembly method, a flat card may be placed at least on a portion of the stationary panel 450 over the sutures before and during folding of the first and second folding panels 460a–b. More particularly, the flat card may be more particularly sized and positioned so as to extend generally from the second transverse fold line 480b to about the first row 456a of the securing mechanisms 402. The flat card also may be sized and positioned so that it extends across the width of the stationary panel 450 and so as to overlay a portion of the face cover member 430, including the first and preferably the third side fold lines 490a,c, and a portion of the cover securing member 440 including the second side fold line 490b. After folding the first and second folding panels 460a–b as described above, the flat card would be removed from underneath the folding panels.

Preferably, before further folding of the package, as well as during the folding process, the sutures 16 are viewed to verify that they are not hanging on or beyond an outside edge.

After folding the first two folding panels 460a–b over the stationary panel 450, the third folding panel 460c or the bottom flap is folded upwardly about the fourth transverse fold line 480d so that the top surface of the third folding panel is disposed over a portion of the second folding panel. In this way, the third folding panel 460c is also over the ends of the sutures or the looped ends of the sutures, thereby covering and thus protecting these ends or looped ends of these sutures.

Following the folding of the three folding panels 460a–c as described above, the cover securing member 440 is folded about the second and sixth side fold lines 490b,f. In this way, the cover securing member tab securing aperture 446 is positioned to receive the face cover member tab 436 or flap. The face cover member 430 is then folded about the first and third side fold lines 490a,c. In this way, the face cover member first side panel 432a forms a part of another side of the package 400 and the face cover member center panel 434 is positioned over a portion of the stationary panel 450. The face covet member second side panel 432b and the tab 436 also are folded about the fourth and fifth side fold lines 490d–e and the tab or flap is tucked or inserted into the tab receiving aperture 446. Additionally, the face cover member second side member 432b forms a portion of another side of the package 400. The face cover member 430 thus folded forms a cover for a bottom of the package 400 such as that shown in FIG. 7C.

When the three folding panels 460a–c are folded and secured under the face cover member 430, opposing surfaces of the stationary panel 450 and the first folding panel 460a and the opposing surface of the second and third folding panels 460b–c, are preferably arranged so the opposing surfaces of each pair are at an angle with respect to each other. In this way, the suture 16 or flexible component disposed between these opposing surfaces should not bind nor have a drag imposed thereon during the withdrawal of the suture or flexible member from the package 400.

Figure 7D:
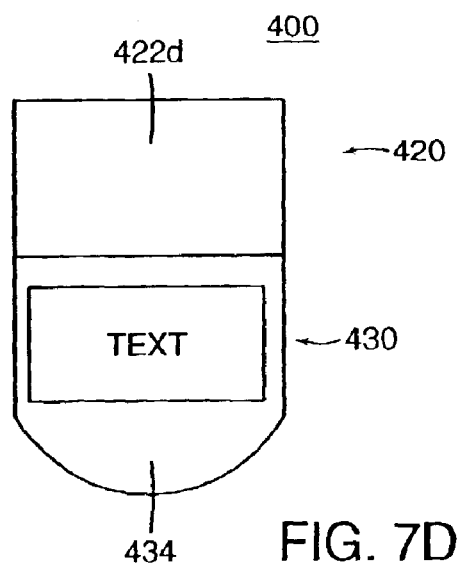

As noted above, the face cover member 430 when so folded does not cover a top portion of the stationary panel 450 so a portion of each suture 16 and each needle 14 remains exposed. As described above, the handle/cover member 420 is folded about certain of the transverse fold lines 480e–j contained within the handle/cover member and the edge, formed by the folding of the HCM fifth panel 422e about the eighth transverse fold line 480h, is tucked under the face cover member 430. In this way, the so-folded handle/cover member 420 forms a cover for the top of the package 300. An example of such a closed package is shown in FIG. 7D.

After the package 400 has been so assembled, the closed and loaded package is placed and sealed in a pouch, such as a tyvek pouch, and sterilized as needed. It is within the scope of the present invention for one or more packages 400 to be stored in a single pouch for shipment and storage at the host facility (e.g., hospital). The package of the present invention yields a package or carrier that provides a compact configuration allowing for convenient box size storage in the host facility (e.g., hospital). The compact configuration also allows for a convenient box size as compared to prior art packages or carriers for purposes of shipping.

The use of any of the above-described packages according to the present invention as well as the advantageous benefits for such a package can be best understood from the following discussion in conjunction with FIGS. 1–6 and 8. Reference also should be made to any of FIGS. 1–6 and the discussion therefore, for further details regarding the construction of any of the features referred to herein and not explicitly described in the following. Although the package 200 according to the third embodiment is illustrated in FIGS. 8A,B this is exemplary or illustrative, as it is within the scope of the present invention for any package according to the present invention to be used in the following manner.

The package 200 is removed from the sterile pouch by the user, such as a scrub nurse for its use in a surgical procedure. The scrub nurse, surgeon or other user opens the package 200 and folds the handle/cover member 20 behind the stationary panel 250 to place the HCM seventh panel 22g proximate the face cover member extension segment 33 thereby forming a handle for the package. As noted above, such a remotely located handle yields a package configuration where the user's grasping of the handle does not lead to possible problems while withdrawing the sutures or flexible member from the open package. As also noted above, a handle extension can be secured to the handle so as to allow the package 200 to be located a distance away from the user holding the package during the medical or surgical procedure.

The folding of the handle/cover member 20 to form the package handle also results in the needles 14 or medical devices being presented to the user, scrub nurse or surgeon so they can be easily removal from package without entangling the sutures 16 or pledgets 18. In particular, this folding sets up the needles 14 so they extend outwardly beyond the confines of the package (see FIG. 8B) thereby providing easy access to the needles, for example by a needle holder. As also indicated above, this folding back of the handle/cover member 20 yields a package configuration that eliminates or minimizes the potential for crushing of or compressing the package during normal use while the needles 14 and sutures 16 are being removed, which might inhibit or restrict suture delivery.

Additionally, the mounting of the double-armed sutures in the package 200 in conjunction with the above described presentation of the needles 14 within the package yields a configuration where the surgeon or scrub nurse can easily withdraw the needles and sutures 16 in either a left to right or right to left direction without entangling the sutures as they are being withdrawn. Thus, the package 200 can be positioned near the surgeon at a more convenient location than would be possible if they could only be removed in one direction.

The open package 200 is positioned in close proximity to the surgeon and the surgical incision/field so the needles 14 and sutures 16 can be removed from the packaging. The small compact packaging configuration allows a package according to the present invention to be located within close proximity to the surgeon without interfering with the surgeon's access to the suture or the surgeon's field of view or vision. Additionally, the package configuration allows the sutures 16 to be removed from the package 200 and thus used directly from the package in close proximity to the surgical incision without interfering with the surgeon's access to the suture or the surgeon's field of view or vision. It also is possible, because of the compact nature of the package of the present invention, to locate the package in the sterile field without significantly affecting the surgeon's view of access.

The surgeon or scrub nurse removes each needle 14 and suture 16 in turn from the package 200 until all the sutures are withdrawn from the package. If further suturing is required, then the scrub nurse opens another package 200, folds back the handle/cover member to form a handle and locates the open package in proximity to the surgical incision or as otherwise described above. This process is repeated as and when necessary until further suturing is not required. Thereafter, the surgeon ties off the sutures using known practices and techniques and completes the surgical procedure.

The packages of the present invention are typically intended to be a single-use type of product. As such, a used package(s) would be disposed of in accordance with the practices and techniques known to those skilled in the art for the proper disposal of items such as those which are used in a given surgical procedure.

The through apertures 52, 104 as shown in the drawings figures are illustrated as being circular or rectilinear in cross-section. However, the through apertures are not limited to the illustrated geometric configurations. Rather, it is within the scope of the present invention for the through apertures to have any geometric configuration or shape including circular, oval, rectilinear, square, polygonal, triangular or other shape through which a suture strand can slidably pass.

Also, a package can be configured with a combination of the above described methods or mechanisms for locally securing the flexible component or suture to the flat unit. For example, the first row can consist of at least one securing mechanism 202 including a through aperture 204 and corresponding tab 206 and /or the second and third rows can be arranged so as to consist of the through aperture pairs as illustrated in FIGS. 1–4.

Although a preferred embodiment of the invention has been described using specific terms, such description is for illustrative purposes only, and it is to be understood that changes and variations may be made without departing from the spirit or scope of the following claims.

What is claimed is:

1. A medical device package that releasably holds therein one or more medical devices, each medical device having a flexible member, the medical device package comprising a support unit, the support unit including a handle panel, wherein:

the handle panel is oriented on the support unit to enable the handle panel to be selectively movable between an open position and a closed position; and the handle panel is oriented on the support unit so that when the handle panel is disposed in the closed position, the handle panel forms a cover that protects a portion of the one or more medical devices therein and wherein the handle panel is oriented on the support unit so that when the handle panel is in the open position, at least a portion of the one or more medical devices is exposed and extends beyond an end of the package and the handle panel; and the support unit further includes a stationary panel and a plurality of folding panels wherein the plurality of folding panels are foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel along an axis transverse to the movement of the handle panel between the open and closed positions and a second folding panel is foldable about the first folding panel along an axis transverse to the movement of the handle panel between the open and closed positions.

2. The medical device package of claim 1, wherein the handle panel is oriented on the support unit such that when the handle panel is disposed in the open position, a handle member is formed for holding the package.

3. The medical device package of claim 2, wherein the handle member that is formed for holding the package is formed remote from where the one or more medical devices are being releasably retained within the package.

4. The medical device package of claim 1,
wherein the support unit further includes a plurality of securing members being arranged so as to from at least two rows, each row being transverse to a long axis of the support unit and having at least one securing member that locally secures a portion of the medical device flexible member.

5. The medical device package of claim 4, wherein each row includes a plurality of securing members and wherein the plurality of securing members in each row are arranged so as to form a plurality of columns of securing members.

6. The medical device package of claim 5, wherein each securing member comprises a pair of through apertures in the support unit.

7. The medical device package of claim 5, wherein each securing member comprises a through aperture in the support unit and a tab disposed over a portion of the through aperture.

8. The medical device package of claim 4, wherein each securing member comprises a pair of through apertures in the support unit.

9. The medical device package of claim 4, wherein each securing member comprises a through aperture in the support unit and a tab disposed over a portion of the through aperture.

10. The medical device package of claim 4, wherein the support unit further includes three rows of securing members.

11. The medical device package of claim 10, wherein each row includes a plurality of securing members and wherein the plurality of securing members in each row are arranged so as to form a plurality of columns of securing members.

12. The medical device package of claim 4, in which each medical device further includes at least one rigid member being interconnected to the flexible member and wherein:
the support unit further includes a mounting member being configured so as to receive a portion of at least one rigid member of each medical device; and the mounting member is transverse to the support unit long axis and spaced from the one of the plurality of rows of at least one securing member.

13. The medical device package of claim 1, wherein: the support unit further includes a plurality of securing members being arranged so as to form at least a first row and a second row of at least one securing member that locally secures a portion of the medical device flexible member, each row being transverse to a long axis of the support unit;
the first row of at least one securing member is disposed in the stationary panel; and the second row of the at least one securing member is disposed in one of the plurality of folding panels.

14. The medical device package of claim 13, wherein each row includes a plurality of securing members and wherein the plurality of securing members in each row are arranged so as to form a plurality of columns of securing members.

15. The medical device package of claim 14, wherein each securing member comprises a pair of through apertures in the support unit.

16. The medical device package of claim 14, wherein each securing member comprises a through aperture in the support unit and a tab disposed over a portion of the through aperture.

17. The medical device package of claim 13, wherein the support unit further includes a third row of at least one securing member, the third row being disposed in the stationary panel intermediate the first and second rows.

18. The medical device package of claim 17, wherein each row includes a plurality of securing members and wherein the plurality of securing members in each row are arranged so as to form a plurality of columns of securing members.

19. The medical device package of claim 1, in which each medical device further includes at least one rigid member being interconnected to the flexible member and wherein:
the at least one rigid member releasably extends a sufficient distance beyond the end of the package when the handle panel is in the open position to allow the at least one rigid member to be removed therefrom using a medical instrument.

20. The medical device package of claim 1, wherein each of the one or more medical devices is one of a single-stranded suture, a double-stranded suture, a double-armed suture, double-stranded sutures in series or a bundled ligature.

21. A medical device package that releasably holds therein one or more medical devices, each medical device having a flexible member, the medical device package comprising a support unit, the support unit including a handle panel, wherein:
the handle panel is oriented on the support unit to enable the handle panel to be selectively movable between an open position and a closed position;
the handle panel is oriented on the support unit so that when the handle panel is disposed in the closed position the handle panel forms a cover that protects a portion of the one or more medical devices therein and the handle panel is oriented on the support unit so that when the handle panel is in the open position, at least a portion of the one or more medical devices is exposed and extends beyond an end of the package;
the support unit further includes a stationary panel and a plurality of folding panels, wherein the plurality of folding panels are foldable about each other and foldable about the stationary panel so the plurality of folding panels can be folded such that the plurality of folding panels are disposed over a portion of the stationary panel; and
the plurality of folding panels are arranged so a first folding panel is foldable about the stationary panel along an axis transverse to the support unit long axis and a second folding panel is foldable about the first folding panel row along an axis transverse to the support unit long axis.

22. The medical device package of claim 21, wherein the plurality of folding panels are arranged so a third folding panel is foldable about the second folding panel row along an axis transverse to the support unit long axis.

23. The medical device package of claim 22, wherein: the support unit further includes a plurality of securing members being arranged so as to form at least a first row and a second row of at least one securing member, each row being transverse to a long axis of the support unit;
the first row of at least one securing member is disposed in the stationary panel; and the second row of at least one securing member is disposed in the second folding panel.

24. The medical device package of claim 21, wherein: the support unit further includes a plurality of securing members being arranged so as to form at least a first row and a second row of at least one securing member, each row being transverse to a long axis of the support unit;
the first row of at least one securing member is disposed in the stationary panel; and the second row of at least one securing member is disposed in the second folding panel.

25. The medical device package of claim 21, wherein the support unit further includes a face cover member that is foldable about the stationary panel along an axis, the face cover member axis, parallel to the support unit long axis and wherein the face cover member and the handle panel when in the closed position cooperate so as to protect the medical devices within the package.

26. The medical device package of claim 25, wherein; the face cover member includes an extension segment; and a portion of the handle panel is disposed proximal the extension segment when the handle panel is in the open position, whereby the extension segment and the handle panel portion create a handle for holding the package.

27. The medical device package of claim 25, wherein the face cover member, when folded about the face cover member axis, is disposed over the plurality of folding panels folded over a portion of the stationary panel.

28. The medical device package of claim 27, wherein the support unit further includes a face cover member securing mechanism that secures an end of the face cover member to the stationary panel.

29. A medical device kit comprising: at least one medical device, each medical device having a flexible member; a medical device package in which is releasably held the at least one medical device, the medical device package including a support unit having a handle panel, wherein:

the handle panel is oriented on the support unit to enable the handle panel to be selectively movable between an open position and a closed position;

the handle panel is oriented on the support unit so that when the handle panel is disposed in the open position at least a portion of the at least one medical device is exposed and extends beyond an end of the package and the handle panel; and the support unit further includes a stationary panel and a plurality of folding panels wherein the plurality of folding panels are foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel along an axis transverse to the movement of the handle panel between the open and closed positions and a second folding panel is foldable about the first folding panel along an axis transverse to the movement of the handle panel between the open and closed positions.

30. The medical device kit of claim 29, wherein the handle panel is oriented on the support unit so that when handle panel is disposed in the closed position the handle panel forms a cover that protects a portion of the one or more medical devices therein.

31. The medical device kit of claim 29, wherein the handle panel is oriented on the support unit such that when the handle panel is disposed in the open position, a handle is formed for holding the medical device package.

32. The medical device kit of claim 31, wherein the handle panel is oriented on the support unit so that the handle is formed remote from where the one or more medical devices are being releasable held within the medical device package.

33. The medical device kit of claim 29, wherein the support unit further includes a plurality of securing members oriented relative to each other so as to form at least two rows, each row being transverse to a long axis of the support unit and having at least one securing member that locally secures a portion of the medical device flexible member.

34. The medical device kit of claim 33, wherein each row includes a plurality of securing members and wherein the plurality of securing members in each row are arranged so as to form a plurality of columns of securing members.

35. The medical device kit of claim 33, wherein each securing member comprises a pair of through apertures in the support unit, where a portion of the medical device flexible member is successively passed through the pair of through apertures to locally secure the flexible member to the support unit.

36. The medical device kit of claim 33, wherein each securing member comprises a through aperture in the support unit and a tab disposed over a portion of the through aperture, where a portion of the medical device flexible member is passed under the tab to locally secure the flexible member to the support unit.

37. The medical device kit of claim 33, wherein the support unit further includes three rows of securing members.

38. The medical device kit of claim 29, wherein the support unit further includes a stationary panel and a plurality of folding panels, wherein the plurality of folding panels are foldable about each other and foldable about the stationary panel so the plurality of folding panels can be folded such that the plurality of folding panels are disposed over a portion of the stationary panel.

39. The medical device kit of claim 33, in which each medical device further includes at least one rigid member being interconnected to the flexible member and wherein:

the support unit further includes a mounting member being configured so as to receive a portion of at least one rigid member of each medical device; and the mounting member is transverse to the support unit long axis and spaced from the one of the plurality of rows of at least one securing member.

40. The medical device kit of claim 39, wherein the at least one rigid member releasably extends from the mounting member to a location a sufficient distance beyond the end of the medical device package when the handle panel is in the open position to allow the at least one rigid member to be removed therefrom using a medical instrument.

41. The medical device kit of claim 29, wherein: the support unit further includes a plurality of securing members being arranged so as to form at least a first row and a second row of at least one securing member for locally securing a portion of the medical device flexible member, each row being transverse to a long axis of the support unit;

the first row of at least one securing member is disposed in the stationary panel; and the second row of at least one securing member is disposed in one of the plurality of folding panels.

42. The medical device kit of claim 41, wherein each row includes a plurality of securing members and wherein the plurality of securing members in each row are arranged so as to form a plurality of columns of securing members.

43. The medical device kit of claim 41, wherein the support unit further includes a third row of at least one securing member, the third row being disposed in the stationary panel intermediate the first and second rows.

44. The medical device kit of claim 39, wherein at least one medical device is one of a single-stranded suture, a double-stranded suture, a double-armed suture, double-stranded sutures in series or a bundled ligature.

45. A medical device kit comprising: at least one medical device, each medical device having a flexible member, and a medical device package in which is releasably held the at least one medical device, the medical device package including a support unit having a handle panel, wherein:

the handle panel is oriented on the support unit to enable the handle panel to be selectively movable between an open position and a closed position;

the handle panel is oriented on the support unit so that when the handle panel is disposed in the open position at least a portion of the at least one medical device is exposed and extends beyond an end of the package;

the support unit further includes a stationary panel and a plurality of folding panels, wherein the plurality of folding panels are foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel along an axis transverse to the support unit long axis and a second folding panel is foldable about the first folding panel row along an axis transverse to the support unit long axis.

46. The medical device kit of claim 45, wherein the plurality of folding panels are arranged so a third folding panel is foldable about the second folding panel row along an axis transverse to the support unit long axis.

47. The medical device kit of claim 46, wherein: the support unit further includes a plurality of securing members being arranged so as to form at least a first row and a second row of at least one securing member that locally secures a portion of the medical device flexible member, each row being transverse to a long axis of the support unit;

the first raw of at least one securing member is disposed in the stationary panel; and the second row of at least one securing member is disposed in the second folding panel.

48. The medical device kit of claim 45, wherein the support unit further includes a face cover member that is foldable about the stationary panel along an axis, the face cover member axis, parallel to the support unit long axis and wherein the face cover member and the handle panel when in the closed position cooperate so as to protect the medical devices within the medical device package.

49. The medical device kit of claim 48, wherein; the face cover member includes an extension segment; and a portion of the handle panel is disposed proximal the extension segment when the handle panel is in the open position, whereby the extension segment and the handle panel are positioned generally adjacent to each other to create a handle for holding the medical device package.

50. A method for dispensing one or more medical devices, each medical device having a flexible member and at least one rigid member interconnected thereto, from a medical device package for use in a medical procedure, the medical device package including a support unit including a handle panel, the handle panel being configured on the support unit so the handle panel can be selectively disposed in one of an open or a closed position, wherein the method comprises the step of:

positioning the handle panel in the open position such that at least a portion of the at least one rigid member for each medical device is exposed and extends beyond an end of the package; and the support unit further includes a stationary panel and a plurality of folding panels wherein the plurality of folding panels are foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel, along an axis transverse to the movement of the handle panel between the open and closed positions and a second folding panel is foldable about the first folding panel alone an axis transverse to the movement of the handle panel between the open and closed positions.

51. The method of claim 50, wherein said step of positioning further includes creating a handle for holding the medical device package by reconfiguring the handle panel when in the open position.

52. The method of claim 50, further comprising the step of locating the medical device package with the rigid members extending therefrom in close proximity to the field for the medical procedure.

53. The method of claim 52, wherein the medical procedure is a surgical procedure and wherein the step of locating includes locating the medical device package in close proximity to the surgical field.

54. The method of claim 53, wherein the step of locating further includes locating the medical device package in the surgical field.

55. The method of claim 50, further comprising the step of withdrawing each of the one or more medical devices from the medical package.

56. The method of claim 50, wherein the medical device support unit further includes a plurality of securing members arranged so as to form at least two rows, each row having at least one securing member for locally securing a portion of the medical device flexible member, and wherein the method further comprises the step of successively withdrawing the medical device flexible member from the at least one securing member in each row.

57. The method of claim 56, wherein each of the plurality of securing members comprises a pair of through apertures in the support unit, where the flexible member is locally secured by successively passing the flexible member through each aperture of the pair, and wherein the step of withdrawing includes successively withdrawing the flexible member from each pair of through apertures in each row.

58. The method of claim 56, wherein each of the plurality of securing members comprises a through aperture in the support unit and a tab, where the flexible member is locally secured by passing the flexible member beneath the tab, and wherein the step of withdrawing includes successively withdrawing the flexible member from beneath the tab of the through aperture and tab in each row.

59. The method of claim 50, wherein the support unit further includes a mounting member in which is releasably retained a portion of the rigid members, and wherein the step of withdrawing includes withdrawing the rigid member from the mounting member.

60. The method of claim 50, wherein the one or more one medical devices being dispensed from the medical package one of a single-stranded suture, a double-stranded suture, a double-armed suture, double-stranded sutures in series or a bundled ligature.

61. A medical device package that releasably holds therein one or wore medical devices, each medical device having a flexible member, the medical device package comprising a support unit, the support unit including a handle panel and a stationary panel, wherein:

the handle panel is oriented on the support unit to enable the handle panel to be selectively movable between an open position and a closed position; and wherein the support unit further includes a face cover member that is foldable about the stationary panel along an axis, the face cover member axis, parallel to the support unit long axis and wherein the face cover member and the handle panel when in the closed position cooperate so as to protect the medical devices within the package; and wherein the face cover member includes an extension segment; and a potion or the handle panel is disposed proximal the extension segment when the handle panel is in the open position, whereby the extension segment and the handle panel portion create a handle for holding the package.

62. A medical device package that releasably holds therein one or more medical devices, each medical device having a flexible member, the medical device package comprising a Support unit, the support unit including a handle panel, wherein:

the handle panel is oriented on the support unit to enable the handle panel to be selectively movable between an open position and a closed position; and the support unit further includes a stationary panel and a plurality of folding panels wherein the plurality of folding panels arc foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel along an axis transverse to the movement of the handle panel between the open and closed positions and a second folding panel is foldable about the first folding panel along an axis transverse to the movement of the handle panel between the open and closed positions.

63. A medical device package that releasably holds therein one or more medical devices, each medical device having a flexible member, the medical device package comprising a support unit, the support unit including a handle panel, wherein:

the handle panel is oriented on the support unit to enable the handle panel to be selectively movable between an open position and a closed position; and the support unit further includes a stationary panel and a plurality of folding panels wherein the plurality of folding panels are foldable about each other and foldable about the stationary panel so the plurality of folding panels can be folded such that the plurality of folding panels are disposed over a portion of the stationary panel; and the plurality of folding panels are arranged so a first folding panel is foldable about the stationary panel along an axis transverse to the support unit long axis and a second folding panel is foldable about the first folding panel along an axis transverse to the support unit long axis.

* * * * *

UNITED STATES PATENT AND TRADEMARK OFFICE
CERTIFICATE OF CORRECTION

PATENT NO.    : 6,938,755 B2
DATED         : September 6, 2005
INVENTOR(S)   : Braginsky et al.

It is certified that error appears in the above-identified patent and that said Letters Patent is hereby corrected as shown below:

Column 26,
Line 61, please replace "from" with -- form --;

Column 31,
Line 24, please replace "raw" with -- row --;

Column 32,
Line 2, please replace "alone" with -- along --;
Line 54, please replace "wore" with -- more --;

Column 33,
Line 10, please replace "Support" with -- support --;
Line 17, please replace "arc" with -- are --.

Signed and Sealed this

Eighth Day of November, 2005

JON W. DUDAS
*Director of the United States Patent and Trademark Office*